United States Patent [19]

Yoshitaka et al.

[11] Patent Number: 5,219,748

[45] Date of Patent: Jun. 15, 1993

[54] RECOMBINANT HUMAN AND RAT PROTEIN KINASE C POLYPETIDES

[75] Inventors: Ono Yoshitaka, Ikeda; Kurokawa Tsutomu, Kawanishi; Igarashi Koichi, Kyoto; Nishizuka Yasutomi, Ashiya, all of Japan

[73] Assignee: Takeda Chemical Industries, Ltd., Osaka, Japan

[21] Appl. No.: 654,404

[22] Filed: Feb. 8, 1991

Related U.S. Application Data

[63] Continuation of Ser. No. 65,828, Jun. 23, 1987.

[30] Foreign Application Priority Data

| Jun. 27, 1986 | [JP] | Japan | 61-149385 |
| Sep. 18, 1986 | [JP] | Japan | 61-217944 |
| Nov. 28, 1986 | [JP] | Japan | 61-281870 |
| May 25, 1987 | [JP] | Japan | 62-40160 |

[51] Int. Cl.$^5$ .................. C12N 9/12; C12N 15/54
[52] U.S. Cl. .................. 435/194; 435/69.1; 536/23.2
[58] Field of Search .................. 435/194

[56] References Cited

PUBLICATIONS

Knopf et al. (1986) Cell 46:491–502.
Suggs, S. V., et al., 1981, Proceedings, National Academy of Sciences, USA 78: 6613–6617.
Kikkawa, U., et al., 1986, Biochemical and Biophysical Research Communications, 135: 636–643.
Kikkawa, U., et al., 1983, Methods in Enzymology 99: 288–298.
Ballester, R., et al., 1985, Journal of Biological Chemistry 260:15194–15199.
Ohno, S., 1989, *Biotrend* (Tokyo), 1-2: 22–27.
Ono, Y., 1991, in, *Gan Idenshi Keakyu, Saikin No Shimpo*, Igakush, C., Ed., at pp. 138–145.
Housey, et al., Journal of Cellular Biochemistry, Suppl. 10C (1986).
Ullrich, et al., Cold Spring Harbor Symposia on Quantitative Biology, vol. L1:713 (1986).
Ono, et al., FEBS Letters, vol. 203:111 (1986).
Makowske et al., The Journal of Biological Chemistry, vol. 261:13389 (1986).
Ono et al., FEBS Letters, vol. 206:347 (1986).
Housey et al., PNAS, vol. 84:1065 (1987).
Ono et al., Science, vol. 236:1116 (1987).
Kikkawa et al., FEBS Letters, vol. 217:227 (1987).
Coussens et al., DNA, vol. 6:389 (1987).
Nishizuka et al., Science, vol. 233:305 (1986).
Nishizuka, "The Role of Protein Kinase C in Cell Surface Signal transduction and Tumour Promotion", Nature 308: 693 (1984).
Nishizuka, "Studies and Perspectives of Protein Kinase C", Science 233: 305 (1986).
Parker et al., "The Complete Primary Structure of Protein Kinase C–The Major Phorbol Ester Receptor", Science 233: 853 (1986).
Coussens et al., "Multiple, Distinct Forms of Borine and Human Protein Kinase C etc.", Science 233: 859 (1986).
Knopf, et al. "Cloning and Expression of Multiple Protein Kinase C cDNAs", Cell 46: 491 (1986).
Ohno et al., "Tissue-Specific expression of Three Distinct Types of Rabbit Protein Kinase C", Nature 325: 161 (1978).

*Primary Examiner*—Robert A. Wax
*Assistant Examiner*—William W. Moore
*Attorney, Agent, or Firm*—David G. Conlin; David S. Resnick

[57] ABSTRACT

Human protein kinase C and rat protein kinase C, recombinant DNA containing DNA sequence coding for kinase C, a transformant transformed with a vector containing the above recombinant DNA, and the production method of human or rat kinase C by cultivating the transformant are disclosed.

Kinase C is useful as reagent for studying cellular signal transduction mechanism, as diagnostic and inspection agent for disease, for example tumor, resulting from the trouble of cellular signal transduction mechanism, and as screening agent for a preventive agent or medicine to the disease.

7 Claims, 17 Drawing Sheets

| Peptide No. | Amino acid sequence |
|---|---|
| 24 | 5 10<br>Glu-His-Ala-Phe-Phe-Arg-Tyr-Ile-Asp-Trp-<br>Glu-Lys |
| 37 | 5 10<br>Ile-His-Thr-Tyr-Gly -X- Pro-Thr-Phe- X -<br> 15<br>Asp-His- X- Gly-Gly- |
| 49 | 5 10<br>Ser-Val-Asp-Trp-Trp-Ala-Tyr-Gly-Val-Leu-<br> 15 20<br>Leu-Tyr-Glu-Met-Leu-Ala-Gly-Gln-Pro-Pro- |
| 51 | 5 10<br>Ser-Val-Asp-Trp-Trp-Ala-Phe-Gly-Val-Leu-<br> 15 20<br>Leu-Tyr-Glu-Met-Leu-Ala-Gly-Gln-Ala-Pro-<br> 25 30<br>Phe-Glu-Gly-Glu-Asp-Glu-Asp-Glu-Leu-Phe-<br>Gln- |

X; Unidentified

FIG. I

```
GCAGAGATTGCCATCGGTCTTTTCTTCTTGCAGAGCAAGGGCATCATTTACCGTGACCTG      60
AlaGluIleAlaIleGlyLeuPhePheLeuGlnSerLysGlyIleIleTyrArgAspLeu      20

AAACTTGACAACGTGATGCTGGATTCCGAGGGGCACATCAAAATCGCTGACTTTGGCATG     120
LysLeuAspAsnValMetLeuAspSerGluGlyHisIleLysIleAlaAspPheGlyMet      40

TGTAAAGAGAATATCTGGGATGGGGTGACAACCAAGACATTCTGTGGCACTCCAGACTAC     180
CysLysGluAsnIleTrpAspGlyValThrThrLysThrPheCysGlyThrProAspTyr      60

ATTGCCCCAGAGATCATTGCTTATCAGCCCTACGGGAAGTCTGTGGACTGGTGGGCGTTT     240
IleAlaProGluIleIleAlaTyrGlnProTyrGlyLysSerValAspTrpTrpAlaPhe      80

GGAGTCCTGCTGTATGAAATGTTGGCTGGCCAGGCACCTTTTGAAGGGGAGGATGAGGAT     300
GlyValLeuLeuTyrGluMetLeuAlaGlyGlnAlaProPheGluGlyGluAspGluAsp     100

GAACTCTTCCAGTCAATCATGGAGCACAACGTGGCGTATCCCAAGTCCATGTCTAAGGAA     360
GluLeuPheGlnSerIleMetGluHisAsnValAlaTyrProLysSerMetSerLysGlu     120

GCTGTGGCAATCTGCAAAGGGCTAATGACCAAACACCCAGGCAAGCGCCTGGGTTGTGGG     420
AlaValAlaIleCysLysGlyLeuMetThrLysHisProGlyLysArgLeuGlyCysGly     140

CCTGAAGGGGAACGAGACATTAAGGAGCATGCATTTTTCCGGTATATCGACTGGGAGAAA     480
ProGluGlyGluArgAspIleLysGluHisAlaPhePheArgTyrIleAspTrpGluLys     160

CTCGAACGCAAGGAGATTCAGCCACCTTATAAACCAAAAGCTAGAGACAAGCGAGACACC     540
LeuGluArgLysGluIleGlnProProTyrLysProLysAlaArgAspLysArgAspThr     180

TCCAACTTCGACAAAGAGTTCACCAGGCAGCCTGTGGAACTGACTCCCACTGACAAACTC     600
SerAsnPheAspLysGlyPheThrArgGlnProValGluLeuThrProThrAspLysLeu     200
```

FIG. 2-1

```
TTCATCATGAACTTGGACCAAAATGAATTTGCTGGCTTCTCGTATACTAACCCAGAGTTT     660
PheIleMetAsnLeuAspGlnAsnGluPheAlaGlyPheSerTyrThrAsnProGluPhe     220

GTCATTAATGTGTAGGTGAATGCAGATTCCATCGCTGAGCCTGTGTGTAAGGCTGCAGGC     720
ValIleAsnVal    -

TGAATGTCTATTATCAATTCCAGTCTTCCAGGATTCATGGTGCCTCTGTTGGCATCCGTC     780
ATGTGGAGAGCTTGTCTTAGAGGGCTTTTCTTTGTATGTATAGCTTGCTAGTTTGTTTTC     840
TACATTTCAAAATGTTTAGTTTAGAATAAGTGCATTGCCCACTGATAGAGGTACAATTTT     900
CCAGACTTCCAGAAACTCATCCAATGAACCAACAGTGTCAAAACTTAACTGTGTCCGATA     960
CCAAAATGCTTCAGTATTTGTAATTTTTAAAGTCAGATGCTGATGTTCCTGGTCAAAGTT    1020
TTTACAGTTACTCTCGAATATCTCCTTTGAATGCTACCTAAGCATGACCGGTATTTTTAA    1080
AAGTTGTGAGTAAGCTTTGCAGTTACTGTGAACTCTTGTCTCTTGGAGGAAACTTTTTGT    1140
TTAAGAATTGGTATGATTAAATGAATTCATATATGC(A)n
```

FIG. 2-2

FIG. 3

```
        Tyr Ser Ala Gly Gly Asp Leu Met Leu
     AG TAC TCG GCC GGT GGG GAC CTG ATG CTG

His Ile His Ser Asp Val Phe Ser Glu Pro
     CAC ATC CAC AGC GAC GTG TTC TCT GAG CCC

Arg Ala Ile Phe Tyr Ser Ala Cys Val Val
     CGT GCC ATC TTT TAT TCC GCC TGC GTG GTG

Leu Gly Leu Gln Phe Leu His Glu His Lys
     CTG GGC CTA CAG TTT CTT CAC GAA CAC AAG

Ile Val Tyr Arg Asp Leu Lys Leu Asp Asn
     ATC GTC TAC AGG GAC CTG AAG TTG GAC AAT

Leu Leu Leu Asp Thr Glu Gly Tyr Val Lys
     TTG CTC CTG GAC ACC GAG GGC TAC GTC AAG

Ile Ala Asp Phe Gly Leu Cys Lys Glu Gly
     ATC GCA GAC TTT GGC CTC TGC AAG GAG GGG

Met Gly Tyr Gly Asp Arg Thr Ser Thr Phe
     ATG GGC TAT GGG GAC CGG ACC AGC ACA TTC

Cys Gly Thr
     TGT GGG ACC C
```

FIG. 4

```
GCAGAGATTGCCATCGGTCTTTTCTTCTTGCAGAGCAAGGGCATCATTTACCGTGACCTG      60
AlaGluIleAlaIleGlyLeuPhePheLeuGlnSerLysGlyIleIleTyrArgAspLeu      20
AlaCysValValLeuGlyLeuGlnPheLeuHisGluHisLysIleValTyrArgAspLeu

AAACTTGACAACGTGATGCTGGATTCCGAGGGGCACATCAAAATCGCTGACTTTGGCATG     120
LysLeuAspAsnValMetLeuAspSerGluGlyHisIleLysIleAlaAspPheGlyMet      40
LysLeuAspAsnLeuLeuLeuAspThrGluGlyTyrValLysIleAlaAspPheGlyLeu

TGTAAAGAGAATATCTGGGATGGGGTGACAACCAAGACATTCTGTGGCACTCCAGACTAC    180
CysLysGluAsnIleTrpAspGlyValThrThrLysThrPheCysGlyThrProAspTyr      60
CysLysGluGlyMetGlyTyrGlyAspArgThrSerThrPheCysGlyThr
```

|     | Tyr | Ser | Ala | Gly | Gly | Asp | Leu | Met | Leu |
|-----|-----|-----|-----|-----|-----|-----|-----|-----|-----|
| AG  | TAC | TCG | GCC | GGT | GGG | GAC | CTG | ATG | CTG |

| His | Ile | His | Ser | Asp | Val | Phe | Ser | Glu | Pro |
|-----|-----|-----|-----|-----|-----|-----|-----|-----|-----|
| CAC | ATC | CAC | AGC | GAC | GTG | TTC | TCT | GAG | CCC |

| Arg | Ala | Ile | Phe | Tyr | Ser | Ala | Cys | Val | Val |
|-----|-----|-----|-----|-----|-----|-----|-----|-----|-----|
| CGT | GCC | ATC | TTT | TAT | TCC | GCC | TGC | GTG | GTG |
|     |     |     |     |     |     | GCA |     | ATT | GCC |
|     |     |     |     |     |     |     |     |     |     |

| Leu | Gly | Leu | Gln | Phe | Leu | His | Glu | His | Lys |
|-----|-----|-----|-----|-----|-----|-----|-----|-----|-----|
| CTG | GGC | CTA | CAG | TTT | CTT | CAC | GAA | CAC | AAG |
| ATC | GGT | CTT | TTC | TTC | TTG | CAG | AGC | AAG | GGC |

| Ile | Val | Tyr | Arg | Asp | Leu | Lys | Leu | Asp | Asn |
|-----|-----|-----|-----|-----|-----|-----|-----|-----|-----|
| ATC | GTC | TAC | AGG | GAC | CTG | AAG | TTG | GAC | AAT |
| ATC | ATT | TAC | CGT | GAC | CTG | AAA | CTT | GAC | AAC |

| Leu | Leu | Leu | Asp | Thr | Glu | Gly | Tyr | Val | Lys |
|-----|-----|-----|-----|-----|-----|-----|-----|-----|-----|
| TTG | CTC | CTG | GAC | ACC | GAG | GGC | TAC | GTC | AAG |
| GTG | ATG | CTG | GAT | TCC | GAG | GGG | CAC | ATC | AAA |

| Ile | Ala | Asp | Phe | Gly | Leu | Cys | Lys | Glu | Gly |
|-----|-----|-----|-----|-----|-----|-----|-----|-----|-----|
| ATC | GCA | GAC | TTT | GGC | CTC | TGC | AAG | GAG | GGG |
| ATC | GCT | GAC | TTT | GGC | ATG | TGT | AAA | GAG | AAT |

| Met | Gly | Tyr | Gly | Asp | Arg | Thr | Ser | Thr | Phe |
|-----|-----|-----|-----|-----|-----|-----|-----|-----|-----|
| ATG | GGC | TAT | GGG | GAC | CGG | ACC | AGC | ACA | TTC |
| ATC | TGG | GAT | GGG | GTG | ACA | ACC | AAG | ACA | TTC |

| Cys | Gly | Thr |   |
|-----|-----|-----|---|
| TGT | GGG | ACC | C |
| TGT | GGC | ACT | C |

```
AGGCTCTCTCAAACTTCTGCCGCAGCTCTTCATTGCCCTCGCTTCCTTCCGGCGGCACCG      60
GCACATTAAAGTACTCGCCTTCTTCCTGGCTTAGTAACTTGAACCCTCATCTCCTTGAAC     120
CTTCGGGTACTTAGGCGTTCAATCCTTTCTTGGGCACCCGAGGTGCTCATCTTAACGCAC     180
CCCAGGGCCTAGGACAGGGTGCCAGGGGCGCGGCTCAGATCTGTCCAGCGCAGTCTGCGG     240
TCCTCGCGCCGCAGCGTGCGGCTAAGAACACTTGGCTGGGGGGCCTGCGGGTTGCGGTGT     300
GTGTGTATATGTGTGTGTCTGAGTCTGTGTGTGCGTTTGCTGGTGGTGCCGATATGTA      360
AAGCAGCTGGCGGCTCTGGGCGGGGCCTGGGTTCCATGCAAATGAAGGAGGAGGGGCTAC     420
CCTGGGGCTCCGCCTCCCTCCCCCGCAGCTGGGGCCAGCGGTGCCAAGCACAGCTGGACC     480
AGCGGCAGCAGCTGGGCGAGTGACAGCCCAGCAACGCGCGCGCGGCCGCCGCCAGAGCCG     540
GCGCGAAGGGGCAGCGCGGCCCTGCGGTCCCCGGGCGGCAGCAGCGGCCGCCTAGTCCCG     600
CGCCTCTCCGGGCTTACAGCCCCCGGTCCCGCCGCCCCGGGGCCGCCACCTCTCGGGGCT     660
CCCCCCAGTCCCCGCGCGCGCAAGATGGCTGACCCGGCTGCGGGGCCGCCGCCGAGCGAG     720
                                  MetAlaAspProAlaAlaGlyProProProSerGlu   12
GGCGAGGAGAGCACGGTGCGCTTCGCCCGCAAAGGCGCCCTCCGGCAGAAGAACGTGCAC     780
GlyGluGluSerThrValArgPheAlaArgLysGlyAlaLeuArgGlnLysAsnValHis      32
GAGGTGAAGAACCACAAATTCACCGCCCGCTTCTTCAAGCAGCCCACCTTCTGCAGCCAC     840
GluValLysAsnHisLysPheThrAlaArgPhePheLysGlnProThrPheCysSerHis      52
```

FIG. 8-1

```
TGCACCGACTTCATTTGGGGCTTCGGGAAACAGGGATTCCAGTGTCAAGTCTGCTGCTTT     900
CysThrAspPheIleTrpGlyPheGlyLysGlnGlyPheGlnCysGlnValCysCysPhe      72
GTTGTACACAAGCGCTGCCATGAATTCGTCACGTTCTCCTGCCCTGGTGCAGACAAGGGC     960
ValValHisLysArgCysHisGluPheValThrPheSerCysProGlyAlaAspLysGly      92
CCGGCCTCTGATGACCCACGGAGCAAACACAAGTTTAAGATCCACACCTACTCCAGCCCT    1020
ProAlaSerAspAspProArgSerLysHisLysPheLysIleHisThrTyrSerSerPro     112
ACCTTCTGTGACCACTGTGGATCACTGCTGTATGGGCTCATCCACCAGGGGATGAAATGC    1080
ThrPheCysAspHisCysGlySerLeuLeuTyrGlyLeuIleHisGlnGlyMetLysCys     132
GACACCTGTATGATGAATGTCCACAAGCGCTGCGTGATGAACGTCCCCAGCCTCTGTGGC    1140
AspThrCysMetMetAsnValHisLysArgCysValMetAsnValProSerLeuCysGly     152
ACCGACCACACAGAACGCCGTGGCCGCATCTACATCCAGGCCCACATCGACAGGGAGGTC    1200
ThrAspHisThrGluArgArgGlyArgIleTyrIleGlnAlaHisIleAspArgGluVal     172
CTCATCGTTGTTGTAAGAGATGCTAAAAATCTGGTACCTATGGACCCCAACGGCTTGTCA    1260
LeuIleValValArgAspAlaLysAsnLeuValProMetAspProAsnGlyLeuSer       192
GATCCCTACGTAAAACTGAAACTGATCCCTGATCCCAAAAGTGAGAGCAAGCAGAAGACC    1320
AspProTyrValLysLeuLysLeuIleProAspProLysSerGluSerLysGlnLysThr     212
AAGACTATCAAATGCTCCCTCAACCCGGAGTGGAACGAAACCTTCAGATTTCAGCTGAAG    1380
LysThrIleLysCysSerLeuAsnProGluTrpAsnGluThrPheArgPheGlnLeuLys     232
GAATCAGACAAAGACAGAAGACTGTCCGTAGAGATCTGGGATTGGGACCTGACCAGCAGG    1440
GluSerAspLysAspArgArgLeuSerValGluIleTrpAspTrpAspLeuThrSerArg     252
```

FIG. 8-2

```
AATGACTTCATGGGATCTCTGTCGTTTGGGATTTCAGAACTACAGAAAGCCGGAGTGGAT    1500
AsnAspPheMetGlySerLeuSerPheGlyIleSerGluLeuGlnLysAlaGlyValAsp     272

GGCTGGTTCAAGTTACTAAGCCAGGAAGAAGGCGAGTACTTTAATGTGCCGGTGCCGCCG    1560
GlyTrpPheLysLeuLeuSerGlnGluGluGlyGluTyrPheAsnValProValProPro     292

GAAGGAAGCGAGGGCAATGAAGAGCTGCGGCAGAAGTTTGAGAGAGCCAAGATTGGCCAA    1620
GluGlySerGluGlyAsnGluGluLeuArgGlnLysPheGluArgAlaLysIleGlyGln     312

GGTACCAAGGCTCCAGAAGAAAAGACAGCGAACACTATATCCAAATTTGACAACAATGGC    1680
GlyThrLysAlaProGluGluLysThrAlaAsnThrIleSerLysPheAspAsnAsnGly     332

AACAGGGACCGGATGAAACTGACCGATTTTAACTTCCTGATGGTGCTGGGGAAAGGCAGC    1740
AsnArgAspArgMetLysLeuThrAspPheAsnPheLeuMetValLeuGlyLysGlySer     352

TTTGGCAAGGTCATGCTCTCAGAGCGGAAGGGTACAGATGAACTCTATGCCGTGAAGATC    1800
PheGlyLysValMetLeuSerGluArgLysGlyThrAspGluLeuTyrAlaValLysIle     372

CTGAAGAAAGATGTGGTGATCCAAGATGACGATGTGGAGTGCACAATGGTGGAGAAGAGG    1860
LeuLysLysAspValValIleGlnAspAspAspValGluCysThrMetValGluLysArg     392

GTGCTGGCCCTGCCTGGGAAGCCCCCATTCCTGACTCAGCTCCATTCCTGCTTCCAGACC    1920
ValLeuAlaLeuProGlyLysProProPheLeuThrGlnLeuHisSerCysPheGlnThr     412

ATGGACCGCCTCTACTTTATGATGGAGTATGTGAACGGGGGTGACCTCATGTACCACATC    1980
MetAspArgLeuTyrPheMetMetGluTyrValAsnGlyGlyAspLeuMetTyrHisIle     432

CAACAAGTTGGCCGTTTCAAGGAGCCCCATGCTGTATTTTACGCTGCAGAGATTGCCATC    2040
GlnGlnValGlyArgPheLysGluProHisAlaValPheTyrAlaAlaGluIleAlaIle     452
```

FIG. 8-3

```
GGTCTTTTCTTCTTGCAGAGCAAGGGCATCATTTACCGTGACCTGAAACTTGACAACGTG    2100
GlyLeuPhePheLeuGlnSerLysGlyIleIleTyrArgAspLeuLysLeuAspAsnVal     472

ATGCTGGATTCCGAGGGGCACATCAAAATCGCTGACTTTGGCATGTGTAAAGAGAATATC    2160
MetLeuAspSerGluGlyHisIleLysIleAlaAspPheGlyMetCysLysGluAsnIle     492

TGGGATGGGGTGACAACCAAGACATTCTGTGGCACTCCAGACTACATTGCCCCAGAGATC    2220
TrpAspGlyValThrThrLysThrPheCysGlyThrProAspTyrIleAlaProGluIle     512

ATTGCTTATCAGCCCTACGGGAAGTCTGTGGACTGGTGGGCGTTTGGAGTCCTGCTGTAT    2280
IleAlaTyrGlnProTyrGlyLysSerValAspTrpTrpAlaPheGlyValLeuLeuTyr     532

GAAATGTTGGCTGGCCAGGCACCTTTTGAAGGGGAGGATGAGGATGAACTCTTCCAGTCA    2340
GluMetLeuAlaGlyGlnAlaProPheGluGlyGluAspGluAspGluLeuPheGlnSer     552

ATCATGGAGCACAACGTGGCGTATCCCAAGTCCATGTCTAAGGAAGCTGTGGCAATCTGC    2400
IleMetGluHisAsnValAlaTyrProLysSerMetSerLysGluAlaValAlaIleCys     572

AAAGGGCTAATGACCAAACACCCAGGCAAGCGCCTGGGTTGTGGGCCTGAAGGGGAACGA    2460
LysGlyLeuMetThrLysHisProGlyLysArgLeuGlyCysGlyProGluGlyGluArg     592

GACATTAAGGAGCATGCATTTTTCCGGTATATCGACTGGGAGAAACTCGAACGCAAGGAG    2520
AspIleLysGluHisAlaPhePheArgTyrIleAspTrpGluLysLeuGluArgLysGlu     612

ATTCAGCCACCTTATAAACCAAAAGCTTGTGGGCGAAACGCTGAAAACTTCGACCGGTTT    2547 (2580)
IleGlnProProTyrLysProLysAlaCysGlyArgAsnAlaGluAsnPheAspArgPhe     621  (632)
                                   622

TTCACCCGCCATCCACCAGTCCTAACACCTCCTGACCAGGAAGTCATCAGGAATATTGAC    2547 (2640)
PheThrArgHisProProValLeuThrProProAspGlnGluValIleArgAsnIleAsp     621  (652)
```

FIG. 8-4

| | | |
|---|---|---|
| CAATCAGAATTCGAAGGATTTTCCTTTGTTAACTCTGAATTTTTAAAACCCGAAGTCAAG | 2547 | (2700) |
| GlnSerGluPheGluGlyPheSerPheValAsnSerGluPheLeuLysProGluValLys | 621 | (672) |
| AGCTAAGTAGATCTGTAGACCTCCGTCCTTCATTTCTGTCATTCAAGCTCAACAGCTATC | 2547 | (2760) |
| SerEND | 621 | (673) |
| ATGAGAGACAAGCGAGACACCTCCAACTTCGACAAAGAGTTCACCAGGCAGCCTGTGGAA | 2604 | (2820) |
| ArgAspLysArgAspThrSerAsnPheAspLysGlyPheThrArgGlnProValGlu | 640 | (692) |
| 622 | | |
| CTGACTCCCACTGACAAACTCTTCATCATGAACTTGGACCAAAATGAATTTGCTGGCTTC | 2664 | (2880) |
| LeuThrProThrAspLysLeuPheIleMetAsnLeuAspGlnAsnGluPheAlaGlyPhe | 660 | (712) |
| TGCTATACTAACCCAGAGTTTGTCATTAATGTGTAGGTGAATGCAGATTCCATCGCTGAG | 2724 | (2940 |
| SerTyrThrAsnProGluPheValIleAsnValEND | 671 | (723) |
| CCTGTGTGTAAGGCTGCAGGCTGAATGTCTATTATCAATTCCAGTCTTCCAGGATTCATG | 2784 | (3000) |
| GTGCCTCTGTTGGCATCCGTCATGTGGAGAGCTTGTCTTAGAGGGCTTTTCTTTGTATGT | 2844 | (3060) |
| ATAGCTTGCTAGTTTGTTTTCTACATTTCAAAATGTTTAGTTTAGAATAAGTGCATTGCC | 2904 | (3120) |
| CACTGATAGAGGTACAATTTTCCAGACTTCCAGAAACTCATCCAATGAACCAACAGTGTC | 2964 | (3180) |
| AAAACTTAACTGTGTCCGATACCAAAATGCTTCAGTATTTGTAATTTTTAAAGTCAGATG | 3024 | (3240) |
| CTGATGTTCCTGGTCAAAGTTTTTACAGTTACTCTCGAATATCTCCTTTGAATGCTACCT | 3084 | (3300) |
| AAGCATGACCGGTATTTTTAAAAGTTGTGAGTAAGCTTTGCAGTTACTGTGAACTCTTGT | 3144 | (3360) |

FIG. 8-5

CTCTTGGAGGAAACTTTTTGTTTAAGAATTGGTATGATTAAATGAATTCATATATGC (A) n

MetAlaAspValTyrProAlaAsnAspSerThrAlaSerGlnAspValAlaAsnArgPhe
   ATGGCTGACGTTTACCCGGCCAACGACTCCACGGCGTCTCAGGACGTGGCCAACCGCTTC

AlaArgLysGlyAlaLeuArgGlnLysAsnValHisGluValLysAspHisLysPheIle
   GCCCGCAAAGGGGCGCTGAGGCAGAAGAACGTGCATGAGGTGAAAGACCACAAATTCATC

AlaArgPhePheLysGlnProThrPheCysSerHisCysThrAspPheIleTrpGlyPhe
   GCCCGCTTCTTCAAGCAACCCACCTTCTGCAGCCACTGCACCGACTTCATCTGGGGGTTT

GlyLysGlnGlyPheGlnCysGlnValCysCysPheValValHisLysArgCysHisGlu
   GGAAAACAAGGCTTCCAGTGCCAAGTTTGCTGTTTTGTGGTTCACAAGAGGTGCCATGAG

PheValThrPheSerCysProGlyAlaAspLysGlyProAspThrAspAspProArgSer
   TTTGTTACTTTCTCTTGTCCGGGTGCGGATAAGGGACCTGACACTGATGACCCCAGAAGC

LysHisLysPheLysIleHisThrTyrGlySerProThrPheCysAspHisCysGlySer
   AAGCACAAGTTCAAAATCCACACCTATGGAAGCCCTACCTTCTGTGATCACTGTGGGTCC

LeuLeuTyrGlyLeuIleHisGlnGlyMetLysCysAspThrCysAspMetAsnValHis
   CTGCTCTACGGACTTATCCACCAAGGGATGAAATGCGACACCTGCGACATGAATGTTCAC

LysGlnCysValIleAsnValProSerLeuCysGlyMetAspHisThrGluLysArgGly
   AAGCAGTGCGTGATCAATGTCCCCAGCCTCTGCGGAATGGATCACACAGAGAAGAGGGGG

ArgIleTyrLeuLysAlaGluValThrAspGluLysLeuHisValThrValArgAspAla
   CGGATTTACCTGAAGGCAGAGGTCACAGATGAAAAGCTGCACGTCACCGTACGAGATGCA

LysAsnLeuIleProMetAspProAsnGlyLeuSerAspProTyrValLysLeuLysLeu
   AAAAATCTAATCCCTATGGATCCAAATGGGCTTTCGGATCCTTACGTGAAGCTGAAACTT

IleProAspProLysAsnGluSerLysGlnLysThrLysThrIleArgSerThrLeuAsn
   ATTCCTGACCCCAAGAATGAGAGCAAACAGAAAACCAAAACCATCCGATCCACACTGAAC

ProGlnTrpAsnGluSerPheThrPheLysLeuLysProSerAspLysAspArgArgLeu
   CCTCAGTGGAATGAGTCCTTCACGTTCAAATTAAAACCTTCAGACAAAGACCGGCGACTG

SerValGluIleTrpAspTrpAspArgThrThrArgAsnAspPheMetGlySerLeuSer
   TCCGTAGAAATCTGGGACTGGGATCGGACGACACGGAATGACTTCATGGGCTCCCTTTCC

PheGlyValSerGluLeuMetLysMetProAlaSerGlyTrpTyrLysLeuLeuAsnGln
   TTCGGCGTCTCAGAGCTGATGAAGATGCCAGCCAGTGGATGGTACAAGTTGCTCAACCAA

GluGluGlyGluTyrTyrAsnValProIleProGluGlyAspGluGluGlyAsnValGlu
   GAGGAGGGTGAATACTACAATGTGCCCATTCCAGAAGGAGATGAAGAAGGCAACGTGGAA

LeuArgGlnLysPheGluLysAlaLysLeuGlyProAlaGlyAsnLysValIleSerPro
   CTCAGGCAGAAGTTCGAGAAAGCCAAGCTGGGCCCCGCTGGAAACAAAGTCATCAGCCCT

SerGluAspArgLysGlnProSerAsnAsnLeuAspArgValLysLeuThrAspPheAsn
   TCAGAAGACAGGAAGCAGCCATCTAACAACCTGGACAGGGTGAAACTCACAGACTTCAAC
```

FIG. 13-1

```
PheLeuMetValLeuGlyLysGlySerPheGlyLysValMetLeuAlaAspArgLysGly
TTCCTCATGGTGCTGGGGAAGGGGAGTTTTGGAAAGGTGATGCTTGCTGACAGGAAGGGA

ThrGluGluLeuTyrAlaIleLysIleLeuLysLysAspValValIleGlnAspAspAsp
ACAGAGGAGCTGTACGCCATCAAAATCCTGAAGAAGGACGTGGTGATCCAGGATGACGAC

ValGluCysThrMetValGluLysArgValLeuAlaLeuLeuAspLysProProPheLeu
GTGGAGTGCACCATGGTGGAGAAGCGGGTTCTGGCCCTGCTCGACAAGCCCCCGTTCCTG

ThrGlnLeuHisSerCysPheGlnThrValAspArgLeuTyrPheValMetGluTyrVal
ACACAGCTGCACTCCTGCTTCCAGACAGTGGACCGGCTGTACTTCGTCATGGAATACGTC

AsnGlyGlyAspLeuMetTyrHisIleGlnGlnValGlyLysPheLysGluProGlnAla
AACGGTGGGGACCTCATGTACCACATTCAGCAAGTCGGAAAATTTAAGGAGCCACAAGCA

ValPheTyrAlaAlaGluIleSerIleGlyLeuPhePheLeuHisLysArgGlyIleIle
GTATTCTATGCAGCCGAGATCTCCATCGGACTGTTCTTTCTTCACAAAAGAGGAATCATT

TyrArgAspLeuLysLeuAspAsnValMetLeuAspSerGluGlyHisIleLysIleAla
TACAGGGATCTGAAGCTGGACAACGTCATGCTGGACTCAGAAGGGCATATCAAAATCGCC

AspPheGlyMetCysLysGluHisMetMetAspGlyValThrThrArgThrPheCysGly
GACTTCGGGATGTGCAAGGAACACATGATGGACGGGGTCACGACCAGGACCTTCTGTGGG

ThrProAspTyrIleAlaProGluIleIleAlaTyrGlnProTyrGlyLysSerValAsp
ACTCCGGATTACATTGCCCCAGAGATAATCGCTTACCAGCCATATGGAAAGTCTGTGGAC

TrpTrpAlaTyrGlyValLeuLeuTyrGluMetLeuAlaGlyGlnProProPheAspGly
TGGTGGGCGTACGGCGTGCTCCTGTATGAGATGCTAGCTGGGCAGCCTCCGTTCGATGGC

GluAspGluAspGluLeuPheGlnSerIleMetGluHisAsnValSerTyrProLysSer
GAAGACGAAGATGAACTGTTTCAGTCTATAATGGAGCACAATGTGTCCTACCCCAAATCC

LeuSerLysGluAlaValSerIleCysLysGlyLeuMetThrLysHisProAlaLysArg
TTGTCCAAGGAAGCTGTCTCCATCTGCAAAGGGCTTATGACCAAACACCCTGCCAAGCGG

LeuGlyCysGlyProGluGlyGluArgAspValArgGluHisAlaPhePheArgArgIle
CTGGGCTGCGGGCCCGAGGGGGAAAGGGATGTCAGAGAGCATGCCTTCTTTAGGAGGATC

AspTrpGluLysLeuGluAsnArgGluIleGlnProProPheLysProLysValCysGly
GACTGGGAGAAGTTGGAGAACAGGGAGATCCAACCGCCATTCAAGCCCAAAGTGTGCGGC

LysGlyAlaGluAsnPheAspLysPhePheThrArgGlyGlnProValLeuThrProPro
AAAGGAGCAGAAAACTTTGACAAGTTCTTCACACGAGGGCAGCCTGTCTTAACACCACCA

AspGlnLeuValIleAlaAsnIleAspGlnSerAspPheGluGlyPheSerTyrValAsn
GATCAGCTGGTCATCGCTAACATAGACCAGTCTGATTTTGAAGGGTTCTCGTATGTCAAC

ProGlnPheValHisProIleLeuGlnSerAlaValtrm
CCCCAGTTTGTGCACCCAATCTTGCAAAGTGCAGTATGA
```

FIG. 13-2

RECOMBINANT HUMAN AND RAT PROTEIN KINASE C POLYPETIDES

This is a continuation of copending application(s) Ser. No. 07/065,828 filed on Jun. 23, 1987 now abandoned.

BACKGROUND OF THE INVENTION (a) Field of the Invention

The present invention relates to a calcium- and phospholipid-dependent protein phosphorylation enzyme (hereinafter referred to as protein phosphorylation enzyme C or protein kinase C for brevity) and to recombinant DNA technique for the production thereof, especially to rat kinase C and human kinase C.

(b) Description of the Prior Art

Numerous kinds of biologically active substances such as cell growth factors, hormones and neutrotransmitters are known to participate in the exertion of various functions and adaptation phenomena of living organisms. These extracellular signals are exerted through intracellular mediators such as cyclic AMP (cAMP), cyclic GMP (cGMP), diacylglycerol (DG) and calcium ($Ca^{++}$). It has been revealed that DG is produced as a result of inositol phospholipid breakdown in cell membranes by a number of hormones and neutrotransmitters which are responsible for the activation of cellular functions. It is considered that the activation of various cellular functions and cellular proliferation are attained by the phosphorylation of various intracellular proteins with a protein kinase C enzyme which is activated by DG in the presence of $Ca^{++}$. Thus, protein kinase C is an enzyme which plays an important role in a mechanism of main information transduction of external signals. The enzyme isolated from rat brains is an acidic protein having an isoelectric point of pH 5.6 and a molecular weight of approximate 77,000. This enzyme is composed of a single peptide having a hydrophobic region serving as a binding site to cell membranes and a hydrophilic region in which the active center exists. The protein kinase C is normally in an inactive form but is activated by calcium, phosphatidyl-serine and DG. ATP is known to serve as the phosphoric acid donor.

Thus, the protein kinase C performs the transduction of extracellular signals into cells through the phosphorylation of proteins as a protein kinase and, therefore, it is one of the indispensable enzymes in studying of extracellular signal reception and transduction mechanism and is a very valuable reagent. The enzyme is also activated directly by tumor-promoting phorbol esters. Phorbol esters are known not only to cause promotion of carcinogenesis but also to take part in various biological reactions such as mitosis and differentiation of cells, induction of enzymes and acceleration of lipid metabolism. In these circumtances, there is a great possibility that the protein kinase C becomes an important index enzyme in diseased cells or tumor cells resulting from troubles in cellular signal transduction mechanism and that antibodies to the protein kinase C are used as diagnostic and inspection reagents. For these purposes, it is essential to provide a large amount of human protein kinase C. However, natural human protein kinase C is present only in a small amount. Further, to obtain the human protein kinase C from human tissues involves various problems and is extremely difficult. Therefore, the amino acid sequence of the human protein kinase C and the DNA sequence of the human protein kinase C gene have not been determined yet.

On the other hand, protein kinase C may be derived from readily available animal parts, such as, for example, a protein kinase C purified from rat brains. However, the amino acid sequence and the gene DNA sequence of rat protein kinase C has not been determined yet. It is also very difficult to obtain rat protein kinase C in a large amount.

As described above, there are remaining a number of unknown points with respect to the properties, the amino acid sequence and the gene of human protein kinase C and rat protein kinase C. Therefore, it is highly desired to elucidate the gene coding for the protein kinase C and to provide a production method for the protein as a reagent and an inspecting agent by gene recombinant techniques.

SUMMARY OF THE INVENTION

Animals having resemblance to human have proteins which show a high homology with human proteins in amino acid sequence. A greater part of the differences in amino acids would be introduced by only one point mutuation of codons. Thus, the present inventors have purified a protein kinase C derived from rat brain which is easily available material, determined the amino acid sequence thereof and elucidated the DNA sequence of the rat protein kinase C gene. The DNA sequence of the rat protein kinase C gene is described in detail in Examples 1, 2 and 4 and the DNA sequence and the amino acid sequence deduced from the DNA sequence is shown in FIGS. 2 and 8.

Although a number of DNA sequences are possible for the DNA sequence of the cloned rat protein kinase C gene by degeneracy of codons, a portion of the DNA sequence is assumed to resemble the DNA sequence of the human protein kinase C. Based on this assumption, the present inventors have first cloned the rat protein kinase C gene and have cloned the human protein kinase C gene from human cells using a cDNA obtained from the cloned rat protein kinase C gene as a DNA probe. By constructing a recombinant DNA having the human protein kinase C gene, and by cultivating a transformant transformed with the recombinant DNA, the human protein kinase C is produced. With the foregoing findings in view, the present inventors have made a further study and have completed the present invention.

The present invention provides:

(1) a human protein kinase C (I) which is a polypeptide comprising the following amino acid sequence:

Tyr-Ser-Ala-Gly-Gly-Asp-Leu-Met-Leu-His-Ile-His-Ser-Asp -Val-Phe-Ser-Glu-Pro-Arg-Ala-Ile-Phe-Tyr-Ser-Ala-Cys-Val -Val-Leu-Gly-Leu-Gln-Phe-Leu-His-Glu-His-Lys-Ile-Val-Tyr -Arg-Asp-Leu-Lys-Leu-Asp-Asn-Leu-Leu-Leu-Asp-Thr-Glu-Gly -Tyr-Val-Lys-Ile-Ala-Asp-Phe-Gly-Leu-Cys-Lys-Glu-Gly-Met -Gly-Tyr-Gly-Asp-Arg-Thr-Ser-Thr-Phe-Cys-Gly-Thr;

a portion thereof which has the same activity; or the polypeptide which is partially substituted in the above amino acid sequence and has the same activity.

(2) a recombinant DNA (II) comprising a nucleotide sequence coding for the human protein kinase C;

(3) a transformant transformed with a vector containing the DNA (II); and (4) a process for the production of human protein kinase C characterized in cultivating a transformant (3) in a culture medium to produce and accumulate the human protein kinase C in the culture and recovering the same.

Further the present invention provides:

(5) A rat protein kinase C which is a polypeptide consisting of the amino acid sequence shown in FIG. 8 or in FIG. 13;

(6) a recombinant DNA (IV) comprising a DNA sequence coding for the rat protein kinase C;

(7) A transformant transformed with a vector containing the DNA (IV); and (8) A process for the production of rat protein kinase C characterized in cultivating a transformat (7) in a culture medium to produce and accumulate the rat kinase in the culture and recovering the same.

BRIEF DESCRIPTION OF THE DRAWINGS:

FIG. 2-1 depicts nucleotides 1-600 of the rat protein kinase C cDNA and amino acids 1-200 deduced from the nucleotide sequence;

FIG. 2—2 depicts nucleotides 601-1177 of the rat protein kinase C cDNA and amino acids 201-224 deduced from the nucleotide sequence;

FIG. 3 is a schematic representation of the restriction enzyme map for the human protein kinase C cDNA;

FIG. 4 shows a nucleotide sequence of a portion of the human protein kinase C cDNA and the deduced amino acid sequence;

FIGS. 5 and 6 show homology relation between the nucleotide sequence of rat protein kinase C cDNA and the deduced amino acid sequence (FIG. 2) and the nucleotide sequence of a portion of the human protein kinase C cDNA and the deduced amino acid sequence (FIG. 4);

FIG. 8 shows the entire nucleotide sequence of type I (β-1) rat brain protein kinase C cDNA and the deduced amino acid sequence, wherein the region in the box shows an additional nucleotide sequence added to the type I (β-1) and the nucleotide sequence thus added is the entire nucleotide sequence of type II (β-2);

FIG. 8-1 depicts nucleotides 1-840 of the type I (β-1) rat brain protein kinase C cDNA and the deduced amino acids 1-52;

FIG. 8-2 depicts nucleotides 841-1440 of the type I (β-1) rat brain protein kinase C cDNA and the deduced amino acids 53-252;

FIG. 8-3 depicts nucleotides 1441-2040 of the type I (β-1) rat brain protein kinase C cDNA and the deduced amino acids 253-452;

FIG. 8-4 depicts nucleotides 2041-2547 of the type I (β-1) rat brain protein kinase C cDNA and the deduced amino acids 453-621 and the boxed region depicts nucleotides (2548-2640) and the deduced amino acids (622-652) of type II (β-2);

FIG. 8-5 depicts nucleotides 2548-3144 of the type I (β-1) rat brain protein kinase C cDNA and the deduced amino acids 622-671 and the boxed region depicts nuleotides (3145-3360) and the deduced amino acid sequence (653-673) of type II (β-2);

FIG. 8-6 depicts nucleotides 3145-3201 of the type I (β-1) rat brain protein kinase C cDNA;

FIG. 9-1 is a scheme for constructing the plasmid pTB648;

FIG. 9-2 is a scheme representing the use of pTB648 in the construction of a plasmid for expressing rat brain protein kinase C in animal cells;

FIG. 13 shows the DNA sequence of rat protein kinase C III (α type) protein coding region and the amino acid sequence deduced from the DNA sequence.

DESCRIPTION OF THE PREFERRED EMBODIMENT

Figure 7:
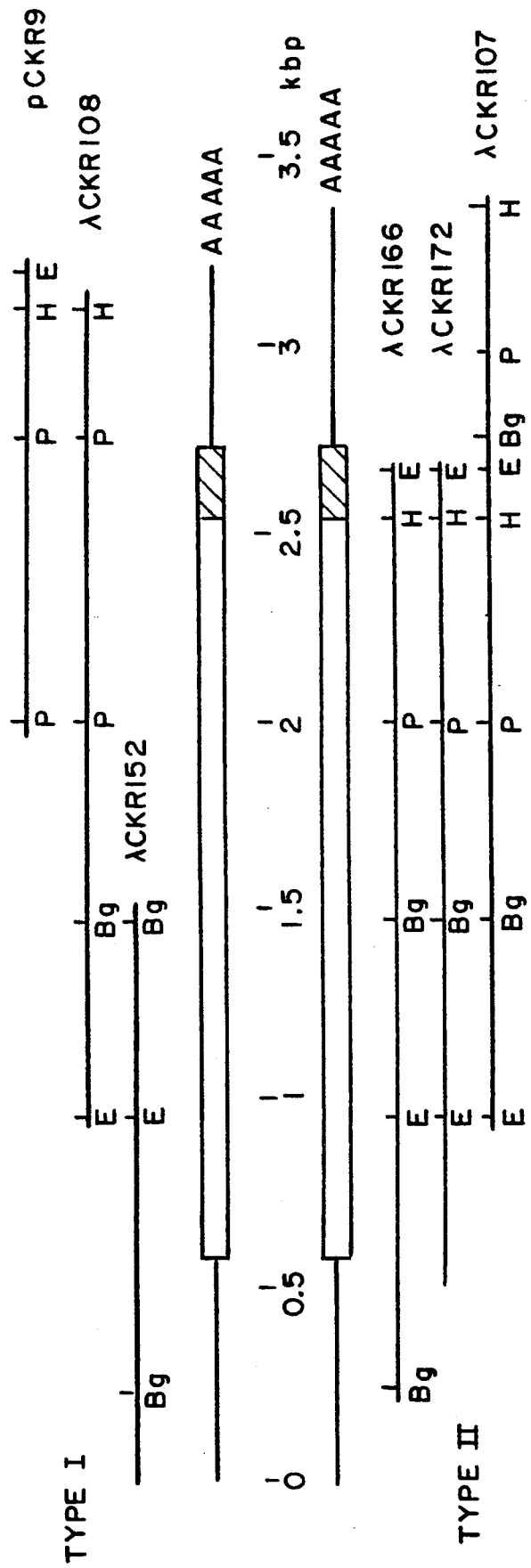
FIG. 7 is a schematic representation showing the manner of overlapping of two types of rat protein kinase C clones obtained in Example 4.

The above described DNA (II) for expression of the human protein kinase C may have preferably the following DNA sequence (III):

AGTACTCGGCCGGTGGGGACCT-
GATGCTGCACATCCACAGC-
GACGTGTTCTC
TGAGCCCCGTGCCATCTTT-
TATTCCGCCTGCGTGGTGCTGGGC-
CTACAGTTT
CTTCACGAACACAAGATCGTCTACAGG-
GACCTGAAGTTGGACAATTTGCTCC
TGGACACCGAGGGCTACGTCAAGATC-
GCAGACTTTGGCCTCTGCAAGGAGGG
GATGGGCTATGGGGACCGGACCAG-
CACATTCTGTGGGACCC.

The human protein kinase C in the DNA and the transformant according to the present invention and in the production process according to the present invention contains as a part thereof the human protein kinase C (I) expressed by the above amino acid sequence.

The above described DNA (IV) for expression of rat protein kinase C may have preferebly the DNA sequence shown in FIG. 8 or in FIG. 13.

An expression vector containing a DNA having a nucleotide sequence coding for the polypeptide of a human protein protein kinase C according to the present invention may be produced by a method including the steps of:

(a) separating an RNA coding for a human protein kinase C, (b) preparing a single strand complementary DNA (cDNA) and then a double strand DNA from the RNA, (c) inserting the complementary DNA into a plasmid, (d) transforming a host with the recombinant plasmid, (e) after cultivating the thus obtained transformant, isolating a plasmid containing the desired DNA from the transformant by any suitable method such as a colony hybridization method using a rat cDNA as probe, (f) cutting out the desired, cloned DNA from the plasmid, and (g) ligating the cloned DNA to a vehicle at a position downstream from the promoter.

The RNA coding for the human protein kinase C may be obtained from various human protein kinase C-producing cell lines such as human brain-derived cells and human fibroblasts. Examples of the human fibroblasts include WI38 (ATCC No. CCL-75) and IMR90 (ATCC No. CCL-186). The cells WI38 and IMR90 are listed in Catalogue of Cell Lines & Hybridomas, 5th edition, 1985, published by The American Type Culture Collection.

As a method of preparing RNA from a human protein kinase C-producing cell line, there may be mentioned the guanidine-thiocyanate method [Chirgwin, J. M., Biochemistry 18, 5294 (1979)].

Using the thus obtained RNA as template, a cDNA is prepared with a reverse transcription enzyme according to a method of, for example, Okayama, H. et al [Molecular and Cellular Biology 2, 161(1982); ibid. 3, 280(1980)]. The resulting cDNA is inserted into a plasmid.

The plasmid into which the cDNA is to be inserted may be, for example, $E.$ $coli$-derived pBR322 [Gene 2, 95(1977)], pBR325 [Gene 4, 121(1978)], pUC12 [Gene 19, 259(1982)]and pUC13 [Gene 19, 259(1982)]and $Bacillus$ $subtilus$-derived pUB110 [Biochemical amd Biophysical Research Communication 112, 678(1983)]. Other plasmids may be used as long as they can be replicated in a host.

As a method for inserting the cDNA into a plasmid, there may be mentioned the method of Maniatis, T. et al disclosed in "Molecular Cloning", Cold Spring Harbor Laboratory, page 239 (1982).

The cDNA-inserted plasmid may be one obtained with the use of a cDNA library (available from Dr. Okayama, National Institute of Child Health and Human Development, Bethesda, U.S.A.) using $E.$ $coli$ x1776 as a host and obtained by inserting a cDNA prepared from human normal diploid cell mRNA into pCD vector [Okayama et al, Molecular Cell. Biology 3, 280(1983)].

With the plasmid thus obtained is then transfected to a suitable host such as a microorganism belonging to the genus Escherichia or Bacillus.

Examples of microorganisms belonging to the genus Escherihcia include $Escherichia$ $coli$ K12DH1 [Proc. Natl. Acad. Sci. U.S.A. 60, 160(1968)], M103 [Nucleic Acids Research 9, 309(1981)], JA221 [Journal of Molecular Biology 120, 517(1978)], HB101 [Journal of Molecular Biology 41, 459(1969)] and C600 [Genetics 39, 440(1954)].

Examples of microorganisms belonging to the genus Bacillus include $Bacillus$ $subtilis$ MI114 [Gene 24, 255(1983)]and 207-21 [Journal of Molecular Biology 95, 87(1984)].

A method for the transformation may be, for example, the calcium chloride method or calcium chloride/rubidium chloride method of Manitatis, T. et al ["Molecular Cloning", Cold Spring Harbor Laboratory, page 249 (1982)].

From the thus obtained transformants, the desired clones are singled out by any known method, for example a colony hybridization method [Gene 10, 63(1980)] and a DNA base sequence determination method [Proc. Natl. Acad. Sci. U.S.A. 74, 560(1977); Nucleic Acids Research 9, 309(1981)].

In the foregoing manner, a microorganism carrying a vector containing a cloned DNA having a nucleotide sequence coding for the human protein kinase C may be obtained.

The plasmid pTB637 contained in $Escherichia$ $coli$ K12DH1/pTB637 obtained in hereinafter described Example 3(1) contains a DNA having a nucleotide sequence coding for the human protein kinase C (I). The nucleotide sequence of the DNA coding for the human protein kinase C (I) is considered to be a part of the DNA. The restriction enzyme cleavage sites of the DNA is shown in FIG. 3. As shown in FIG. 3, the DNA is about 1.2 kbp in its entire length and is cleaved into fragments with restriction enzyme PstI or BamHI.

Then, the plasmid is isolated from the microorganism. As a method of the isolation may be mentioned the alkaline method [Birmboim, H. C. et al, Nucleic Acids Research 1, 1513(1979)].

The plasmid having the cloned DNA having a nucleotide sequence coding for the human protein kinase C is isolated as is, or if desired, is cut out with a restriction enzyme.

The cloned gene is ligated to a vehicle (vector) suitable for expression thereof at a position downstream of its promoter region, thereby to obtain an expression vector.

As the vector, there may be mentioned $E.$ $coli$-derived plasmids such as pBR322, pBR325, pUC12 and pUC13, $Bacillus$ $subtilis$-derived plasmids such as pUB110, pTP5 and pC194, yeast-derived plasmids such as pSH19 and pSH15, bacteriophages such as phage, and animal viruses such as retro virus and vaccinia virus.

The gene may possess at the 5'-terminus ATG serving as a translation initiation codon and at the 3'-terminus TAA, TGA or TAG serving as a translation stop codon. To express the gene, a promoter is linked at its upstream. Any promoter may be used in the present invention as long as it is suitable for the host used for the expression of the gene.

Illustrative of suitable promoters are trp promoter, lac promoter, recA promoter, PL promoter and lpp promoter when the host is a microorganism belonging to the genus Escherichia, SP01 promoter, SP02 promoter and penP promoter when the host belongs to Bacillus, and PH05 promoter, PGK promoter, GAP promoter and ADH promoter when the host is a yeast. Especially preferred is a combination of a microorganism belonging to the genus Escherichia as the host and trp promoter or λ PL promoter as the promoter.

When the host is an animal cell, a promoter derived from SV40 or a promoter of retro virus may be used. The former promoter is especially preferred.

Using the thus constructed vector containing DNA-(II), a transformant is prepared.

As a host, there may be used a microorganism belonging to the genus Escherichia or Bacillus, a yeast or an animal cell.

As the microorganisms belonging to the genus Escherichia or the genus Bacillus the above-described ones may be used. Examples of the suitable yeasts include *Saccaromyces cervisiae* AH22R⁻, NA87-11A and DKD-5D. Examples of suitable animal cells include monkey cells COS-7, Vero, Chinese hamster cell CHO, mouse L cell and human FL cell.

A microorganism belonging to the genus *Escherichia coli* may be transformed according to a method disclosed in, for example, Proc. Natl. Acad. Sci. U.S.A. 69, 2110(1972) or Gene 17, 107(1982). A microorganism belonging to the genus Bacillus may be transformed according to a method disclosed in, for example, Molecular & General Genetics 168, 111(1979). A yeast may be transformed according to a method disclosed in, for example, Proc. Natl. Acad. Sci. U.S.A. 75, 1929(1978). An animal cell may be transformed according to a method disclosed in, for example, Virology 52, 456(1973).

In the manner described above, a transformant transformed with a DNA(II)-containing vector is obtained.

One example of such a transformant is *Escherichia coli* K12DH1/pTB637 obtained in hereinafter described Example 3(1). The microorganism has been deposited with Institute of Fermentation, Osaka (IFO), Japan since Jun. 13, 1986 under the accession number IFO 14510 and also with Fermentation Research Institute, Agency of Industrial Science and Technology, Ministry of International Trade and Industry (FRI) under the accession number FERM P-8815 since Jun. 20 1986, and the deposit has been converted to the deposit under the Budapest Treaty under the accession number FERM BP-1371.

As a medium in which a transformant of a host belonging to the genus Escherichia or Bacillus is cultivated, a liquid medium is appropriate. The liquid medium may be supplemented with a carbon source, a nitrogen source, an inorganic substance and the like required for the growth of the transformant. The carbon source may be, for example, glucose, dextrin, soluble starch or sucrose. The nitrogen source may be, for example, an inorganic or organic substance such as an ammonium salt, a nitrate, corn steep liquor, peptone, casein, meat extract, soybean cake or potato extract. The inorganic substance may be, for example, calcium chloride, sodium dihydrogen phosphate or magnesium chloride. A yeast, vitamin and a growth promoting factor may also be added to the medium. The pH of the medium is preferably in the range of about 6 to 8.

A preferred medium for cultivating a microorganism belonging to the genus Escherichia is M9 medium containing, for example, glucose, casamino acid [Miller, "Journal of Experiments in Molecular Genetics", 431-433, Cold Spring Harbor Laboratory, N.Y. (1972)]. This medium may be supplemented with a suitable agent such as 3β-indolylacrylic acid for the purpose of improving the action of the promoter.

When a microorganism belonging to the genus Escherichia is used as host, the cultivating is generally performed at about 15° to 43° C. for about 3 to 24 hours with, if necessary, aeration and agitation. When a microorganism belonging to the genus Bacillus is used as host, the cultivating is generally performed at about 30° to 40° C. for about 6 to 24 hours with, if necessary, aeration and agitation.

In case where a transformant of a host being yeast is cultivated, Burkholder minimum medium [Bostian, K. L. et al, Proc. Natl. Acad. Sci. U.S.A. 77, 4505(1980)] may be mentioned as an example of the culture medium. The pH of the medium is preferably adjusted to about 5 to 8. The cultivating is generally performed at about 20° to 35° C. for 24 to 72 hours with, if necessary, aeration and agitation.

The medium for cultivating a transformant of a host animal cell may be, for example, MEM medium containing about 5 to 20% of fetal bovine serum [Science 122, 501(1952)], DMEM medium [Virology 8, 396(1959)], RPMI1640 medium [The Journal of the American Medical Association 199, 519(1967)] and 199 medium [Proceeding of the Society for the Biological Medicine 73, 1(1950). The pH of the medium is preferably about 6 to 8. The cultivating is generally performed at about 30° to 40° C. for 15 to 60 hours with, if necessary, aeration and agitation.

From the above culture may be separated and purified the human protein kinase C protein in the following manner.

For extracting the human protein kinase C from the cultured microorganism or cell, there may be suitably adopted a method in which the microorganism or the cell is collected from the culture by any conventional method and is suspended in a buffer containing a protein denaturation agent such as guanidine hydrochloric acid. The suspended microorganism or cell is then disrupted by an ultrasonic wave, lysozyme (and/or freezing-and-thawing), followed by centrifugation to obtain the human protein kinase C protein.

Known separation and purification methods may be suitably combined for the purification of the human protein kinase C protein from the above described supernatant. Such known separation and purification methods include, for example, methods utilizing the solubility, such as salting out and solvent precipition; methods utilizing mainly the difference in molecular weight, such as dialysis, ultrafiltration, gel filtration and SDS-polyacrylamide gel electrophoresis; methods utilizing the difference in ionization, such as ion exchange chromatography; methods utilizing the diffference in hydrophobic property, such as reverse high performance liquid chromatography; and methods utilizing the difference in isoelectric point, such as isoelectric point electrophoresis.

Figures 1, 9:
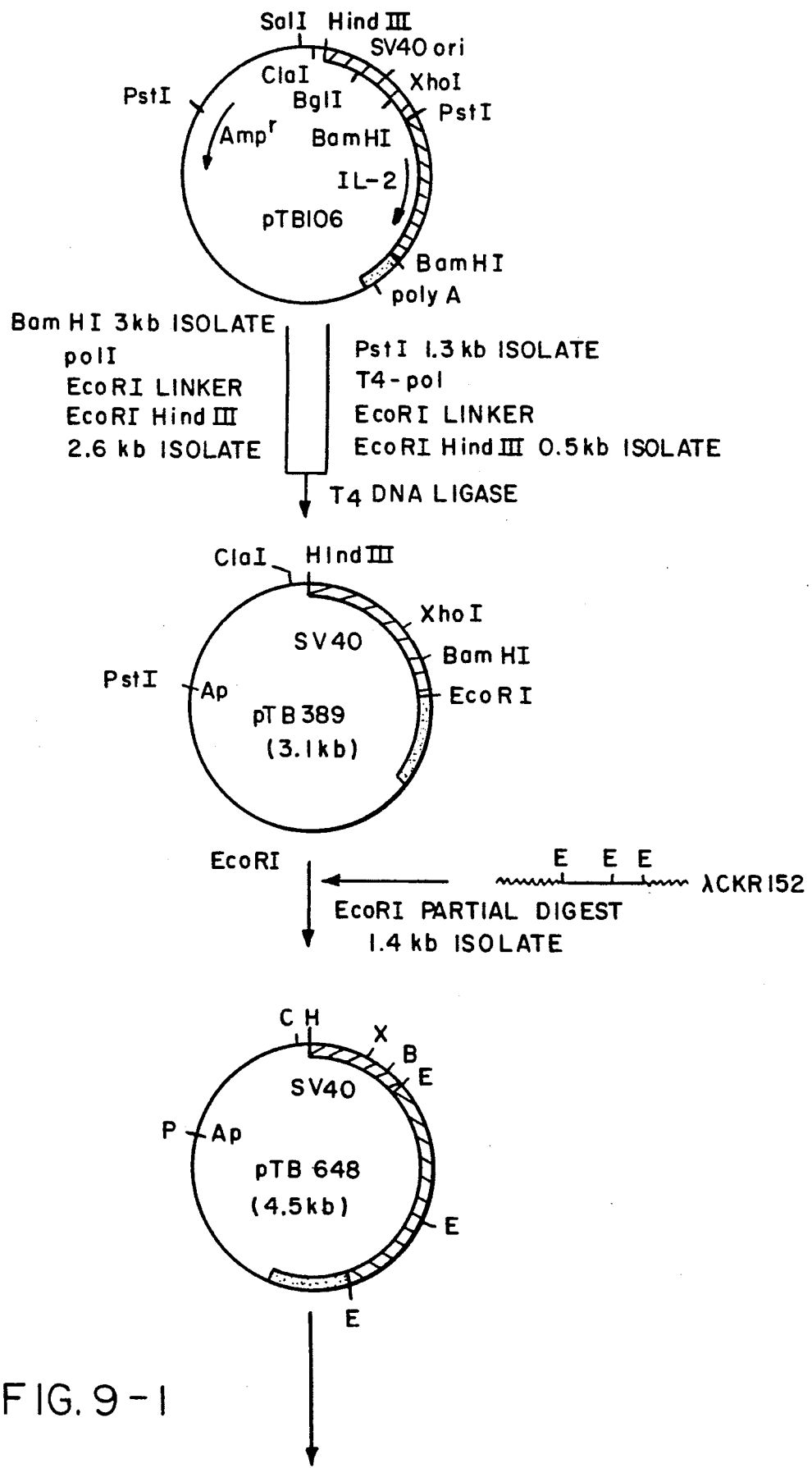
FIG. 1 shows the amino acid sequences of four peptide fractions obtained from rat protein kinase C in Example 1(1)
FIG. 9 is a scheme for constructing the plasmid for expressing rat brain protein kinase C in animal cells.

One example of the human protein kinase C protein obtained by the gene recombinant method according to the present invention is the protein containing the polypeptide having the amino acid sequence shown in FIG. 1. The polypeptide may have Met at its N-terminus.

Activity of the thus obtained human protein kinase C may be assayed in terms of known protein phosphorylation activity.

Various kinds of cells, which originally produce only a small amount of the human protein kinase C or do not at all produce the human protein kinase C, gain an ability to produce a large amount of the human protein kinase C by the transfection with the DNA according to the present invention. And they can produce a large amount of the human protein kinase C.

The expression plasmid of the present invention containing the gene coding for the human protein kinase C protein may be introduced for transformation into various kinds of cells, rendering it possible to let the resultant cells produce the human protein kinase C. Therefore, a large amount of the human protein kinase C may be obtained.

The thus produced human protein kinase C may be used as a reagent or as a diagnosis or inspection material (for example, the amount of protein kinase C used in about 0.001 to 10 μg in one trial) in conjunction with an antibody produced therefrom. For example, the protein kinase C according to the present invention may be used as a reagent for investigating cellular signal transduction mechanisms, as a reagent for diagnosis or inspection of diseases (such as tumor) resulting from a trouble in the cellular signal transduction mechanism, or as a screening agent effective in prevention and curing of the diseases.

In the foregoing have been described in detail the cloning of the human protein kinase C, preparation of the transformant, production of the human protein kinase C protein using the transformant, the usefulness of the protein and the like. These also apply to the rat protein kinase C.

In the present specification and accompanying drawings, abbreviations of bases, amino acids and the like chemicals are based on those according to IUPAC-IUB Commission on Biochemical Nomenclature or those customarily used in the art. Examples of the abbreviations are as follows. Amino acids with optical isomers refer to L-forms except otherwise specifically noted.

| | |
|---|---|
| DNA | Deoxyribonucleic acid |
| cDNA | Complementary deoxyribonucleic acid |
| A | Adenine |
| T | Thymine |
| G | Guanine |
| C | Cytosine |
| RNA | Ribonucleic acid |
| dATP | Deoxyadenosine triphosphate |
| dTTP | Deoxythymidine triphosphate |
| dGTP | Deoxyguanosine triphosphate |
| dCTP | Deoxycytidine triphosphate |
| ATP | Adenosine triphosphate |
| EDTA | Ethylenediamine tetraacetic acid |
| SDS | Sodium dodecylsulfate |
| Gly | Glycine |
| Ala | Alanine |
| Val | Valine |
| Leu | Leucine |
| Ile | Isoleucine |
| Ser | Serine |
| Thr | Threonine |
| Cys | Cysteine |
| Met | Methionine |
| Glu | Glutamic acid |
| Asp | Asparatic acid |
| Lys | Lysine |
| Arg | Arginine |
| His | Histidine |
| Phe | Phenylalanine |
| Tyr | Tyrosine |
| Trp | Tryptophane |
| Pro | Proline |
| Asn | Asparagine |
| Gln | Glutamine |

EXAMPLE

The present invention will be described in more detail hereinafter by way of examples. These examples, however, are not to be construed as limiting the present invention.

The transformant E. coli K12DH1/pTB638 obtained in Example 2 has been deposited at IFO under the accession number IFO 14514 since Jun. 20, 1986 and at FRI under the accession number FERM P-8829 since Jun. 28, 1986, and the deposit has been changed to the deposit according to Budapest Treaty and stored at FRI under the number of FERM BP-1372.

The transformant E. coli K12DH1/pTB652 obtained in Example 4 has been deposited at IFO under the accession number IFO 14539 since Aug. 29, 1986 and at FRI under the accession number FERM P-8958 since Sep. 5, 1986, and the deposit has been changed to the deposit according to Budapest Treaty under the accession number of FERM BP-1373.

The transformant E. coli K12DH1/pTB653 obtained in Example 4 has been deposited at IFO under an accession number IFO 14540 since Aug. 29, 1986 and at FRI under the accession number FERM P-8959 since Sep. 5, 1986, and the deposit has been changed to the deposit according to Budapest Treaty under the accession number of FERM BP-1374.

The transformant E. coli DH1/pTB755 obtained in Example 5 has been deposited at IFO under the accession number IFO 14612 since May 21, 1987, and at FRI under the accession number FERM BP-1382 since May 29, 1987 under the Budapest Treaty.

EXAMPLE 1

(1) Elucidation of Amino Acid Sequence of Rat protein kinase C

From rat brains was extracted a rat protein kinase C in accordance with the method of Kikkawa [J. Biol. Chem 257, 13341(1982)]. There were obtained 2.0 mg of a purified protein kinase C sample from brains of 240 rats. The protein kinase C sample (1.9 mg) was dissolved in 1.9 ml of 50 mM Tris-HCl (pH 9.0) solution containing 6 M urea, to which was added lysylendopeptidase to a concentration of 25 μg/ml, and the mixture was digested at 37° C. for 21 hours. The thus produced peptides were applied on a reverse HPLC column (Micro pak Protein C-18-10, 0.4×30 cm) and followed by an acetonitrile gradient elution to obtain fractions of about 50 peptides. Of these, four peptides (peptides Nos. 24, 37, 49 and 51) were subjected to automated Edman degradation using a vapor phase protein sequencer (Model 470A, Applied Biosystems, Inc.) for the determination of their amino acid sequences.

Phenylthiohydantoin derivatives of amino acids liberated as a result of the Edman degradation were analyzed by HPLC using Micro pak SPC 18-3 column (Varian Associates, Inc.). The amino acid sequence of each of the four peptides was as shown in FIG. 1.

EXAMPLE 2

(1) Preparation of Rat Brain mRNA-Derived cDNA Library

An RNA was extracted from rat brain by the guanidineisothiocyanate method [Chirgwim et al, Biochemistry 18, 5294(1978)]. Poly (A) RNA was purified by oligo dT cellulose column chromatography [Aviv and Leder, Proc. Natl. Acad. Sci. USA 69, 1408(1972)].

Using this poly(A)RNA as a template, cDNA library was constructed with pcDV1 vector and pL1 linker in accordance with the method of Okayama and Berg [Okayama & Berg, Mol. Cell. Biol. 2, 161(1982)]. The vector plasmid containing circularized cDNA was transfected in *E. coli* DH1. Starting from 5 μg of poly-(A)RNA, cDNA library composed of about 5×10⁵ clones and using *E. coli* as a host was obtained.

(2) Isolation of Plasmid Containing Rat Protein Kinase C cDNA and Elucidation of its DNA Sequence The above-described rat cDNA library using *E. coli* DH1 was applied to 10 nitrocellulose filters (Milipore, HATF filter) at about 3×10⁴ clones/filter. Then 20 replica filters (each two being paired) were prepared using these filters as master filters. The *E. coli* on each replica filter was lysed with 0.5N NaOH solution to expose and denature the plasmid DNA, followed by drying for fixation of the DNA on the filter [Grustein, M. & Hogness, D. S., Proc. Natl. Acad. Sci. USA 72, 3961(1975)].

On the basis of the amino acid sequence of the peptides which were determined in Example 1(1), oligonucleotides corresponding to the amino acid sequences were chemically synthesized. Thus

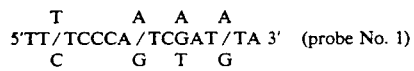

corresponding to the amino acid residues 7-12 of the peptide No. 24 (Tyr-Ile-Asp-Trp-Glu-Lys),

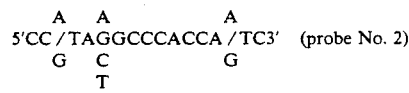

corresponding to the amino acid residues 3-8 of the peptide No. 51 (Asp-Trp-Trp-Ala-Phe-Gly) and

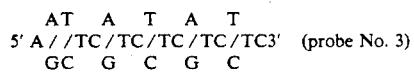

corresponding to the amino acid residues 24-29 of the peptide No. 51 (Glu-Asp-Glu-Asp-Glu-Leu) were each chemically synthesized for use as a screening probe for rat protein kinase C cDNA.

The 5'-terminus of each of the oligonucleotide probes was labeled with $^{32}$P using [γ-$^{32}$P] ATP and T4 polynucleotide kinase.

The labeled probes Nos. 2 and 3 were separately hybridized with the replica filters on which the plasmid DNA was fixed. The hybridization reaction was performed at 42° C. for 16 hours in 10 ml of a 5xSSC (0.15M NaCl, 0.015M sodium citrate), 5xDenhardt's, 0.1% SDS and 100 μg/ml denatured salmon sperum DNA solution containing 10 μCi of the labeled probe. Following the reaction, the filters were washed with a 6xSSC and 0.1% SDS solution three times at room temperature for 30 minutes and twice at 47° C. for 60 minutes in the case of the probe No. 2 and at 43° C. for 60 minutes in the case of the probe No. 3 [Maniatis, M. et al, "Molecular Cloning", Cold Spring Harbor Laboratory, p309(1982)]. A radioautogram was then taken from each washed filter. Radioautograms of each pair of the replica filters were overlaid to explore a strain capable of reacting with both of the two probes. By this method, a strain *E. coli* K12DH1/pTB638 (IFO 14514, FERM BP-1372) capable of reacting with the both probes was taken out from 3×10⁵ colonies.

A plasmid DNA (pTB638) was then extracted from this strain by the alkaline method [Birnboim, H. C. & Doly, J., Nucleic Acids Res. 1, 1513(1979)]. After purification, the DNA was cleaved with restriction enzyme BamHI (manufactured by Takara Shuzo) and the product was electrophoresed on an agarose gel. DNA fragments in the gel were transferred to a nitrocellulose filter (BA85, S & S Inc.) according to the Southern blotting method [Maniatis et al, "Molecular Cloning", Cold spring Harbor Laboratory, pp382 (1982)]. The plasmid DNA fragment on the filter was found to react with all of the above-described oligonucleotide probes.

Figures 2, 9:
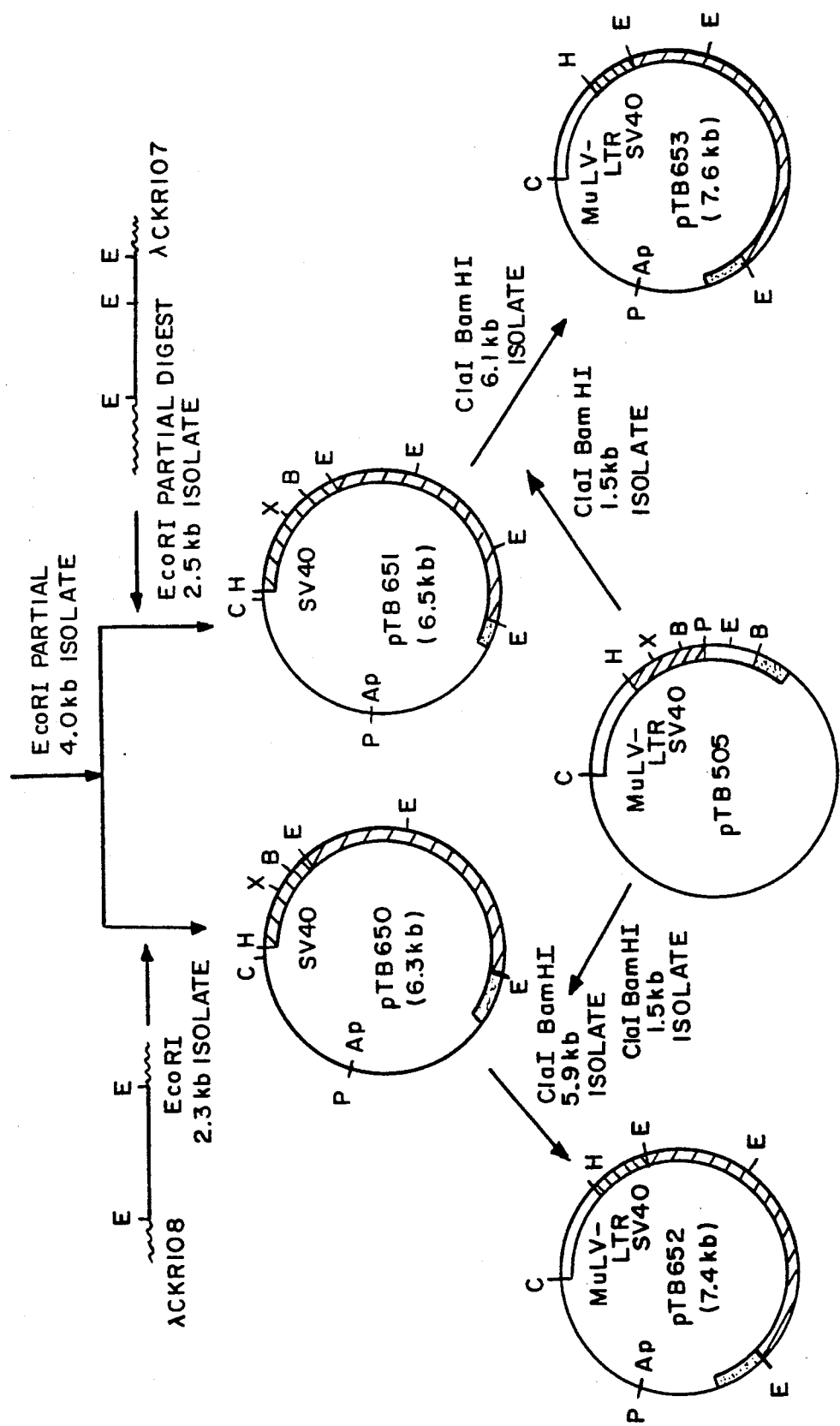
FIG. 2 shows the nucleotide sequence of rat protein kinase C cDNA and the amino acid sequence deduced from the nucleotide sequence.

The nucleotide sequence of a cDNA region of this plasmid DNA was determined by the dideoxynucleotide-chain termination method [Messing, J. et al, Nucleic Acids Res. 9, 309(1981)]. The DNA sequence and the amino acid sequence deduced from the DNA sequence are shown in FIG. 2.

From the sequences shown, it will be seen that the amino acid sequences of the peptides Nos. 24 and 51 determined in Reference Example 1(1) strictly correspond to the nucleotide sequences at Nos. 445-480 and 220-312, respectively. Thus, the plasmid pTB638 was confirmed to be rat protein kinase C cDNA. As the cDNA contained a poly(A) structure, the cDNA was found to have codons of C-terminal region of the protein kinase C and untranslated portion of 3'-terminal region of the mRNA. The rat protein kinase C contains the amino acid sequence shown in FIG. 2 as a part thereof.

EXAMPLE 3

(1) Isolation of Plasmid Containing Human Protein Kinase C cDNA

A cDNA library using as a host *E. coli* x1776 and prepared by inserting a cDNA synthesized from a mRNA of a human foreskin-derived first generation culture cell into pCD vector [See Okayama et al, Mol. Cell. Biol. 3, 280(1983)] was given from Dr. Okayama, National Institute of Child Health and Human Development, Bethesda, U.S.A. A plasmid DNA was extracted from the cDNA library according to the alkaline method [Birnboim, H. C. & Doly, J., Nucleic Acids Res. 1, 1513(1979)] and was transfected in *E. coli* DH1 to obtain a cDNA library using *E. coli* DH1 as a host and composed of about 2×10⁶ clones.

This cDNA library was applied to 12 nitrocellulose filters (HATF filter, Milipore Inc.) at about 5×10⁴ clones/filter. Using these filters as master filters, replica filters were prepared. The *E. coli* on each replica filter was lysed with 0.5 N NaOH solution to expose and denature the plasmid DNA, followed by drying for fixation of the DNA on the filter [Grustein, M. & Hogness, D. S., Proc. Natl. Acad. Sci. USA 72, 3961(1975)].

A DNA fragment of about 0.7 kb obtained by digesting plasmid pTB638 obtained in Example 2-(2) with restriction enzyme PstI was labeled with $^{32}$P using [α-$^{32}$P] αATP and DNA polymerase I by nick translation method [Rigby, P. W. et al, J. Mol. Biol. 113, 237(1977)].

The labeled DNA fragment as a probe was hybridized with the above replica filters on which the plasmid DNA was fixed. The hybridization reaction was performed at 42° C. for 16 hours in 10 ml of a 20% formamide, 5xSSPE, 5xDenhardt's, 0.1% SDS and 100 μg/ml denatured salmon sperum DNA solution containing 5 μCi of the labeled probe. Following the reaction, the filters were washed with a 2xSSC and 0.1% SDS solution three times at room temperature for 30 minutes and twice at 50° C. for 30 minutes [Maniatis, T. et al, "Molecular Cloning", Cold Spring Harbor Laboratory, pp309 (1982)]. A radioautogram was then taken from each washed filter. As a result, a strain *E. coli* K12DH1/pTB637 (IFO 14510, FERM BP1371) capable of reacting with the probe was singled out.

(2) Determination of Nucleotide Sequence of cDNA

From strain *E. coli* K12DH1/pTB637 (IFO 14510, FERM BP1371) obtained in (1) above, a plasmid DNA (pTB637) was extracted and purified by the alkaline method [Birnboim, H. C., Nucleic Acids Res. 1, 1513 (1979)]. The cDNA region of the plasmid DNA is approximately 1.2 Kbp in total length and has the restriction enzyme cleavage map shown in FIG. 3.

A portion of the nucleotide sequence of the cDNA region was determined by the dideoxynucleotide chain termination method [Messing, J. et al, Nucleic Acids Res. 9, 309 (1981)]. The thus determined DNA sequence and the amino acid sequence deduced from the DNA sequence is shown in FIG. 4.

The deduced amino acid sequence shows high homology to that deduced from the rat protein kinase C cDNA shown in Example 2(2), indicating that the cDNA contained in the plasmid pTB637 is human protein kinase C cDNA (See FIGS. 5 and 6). FIG. 5 is a diagram for checking the homology in amino acids, in which the amino acid sequences of FIGS. 2 and 4 are shown with the first amino acid of FIG. 2 being in alignment with the 26th amino acid (Ala) of FIG. 4 and in which the identical amino acid residues are boxed. FIG. 6 is a diagram for checking the homology in DNA sequence, in which the DNA sequences of FIGS. 2 and 4 are shown with the initial codon (G) for the 26th amino acid (Ala) of FIG. 4 being in alignment with the first codon of FIG. 2 and in which the identical nucleotide residues are circled.

Example 4

(1) Preparation of Rat Brain mRNA-Derived cDNA Library

An RNA fragment was extracted from rat brain by the guanidine-isothiocyanate method [Chirgwim et al, Biochemistry 18, 5294(1978)]. Poly (A) RNA was Purified by oligo dT cellulose column chromatography [Aviv and Leder, Proc. Natl. Acad. Sci. USA 69, 1408(1972)].

Using this poly(A)RNA as a template, cDNA library was constructed with phage vector gt10 [Huynh, T. V. et al, "DNA Cloning, A Practical Approach" IRL press, Oxford, p49 (1985)] in accordance with the method of Watson and Jackson [Watson, C. J. & Jackson, J. F., "DNA Cloning, A Practical Approach" IRL press, Oxford, p 49 (1985)]. Starting from 10 µg of poly-(A)RNA, cDNA library composed of about $1.5 \times 10^6$ clones and using *E. coli* C600, HflA (Huynh, T. V. et al, supra) as a host was obtained.

(2) Isolation of Phage Containing Rat Protein Kinase C cDNA and Elucidation of its DNA Base Sequence The above-described phage cDNA library using *E. coli* C600, HflA as a host was applied to 10 soft agar plates at about $1 \times 10^5$ clones/plate and transferred to nitrocellulose filters (HATF filter, Milipore Inc.) and lysed with 0.5N NaOH solution. The resulting exposed and denatured phage DNA was dried for fixation on the plates [Maniatis et al, "Molecular Cloning", Cold Spring Harbor Laboratory, p320(1982)].

*E. coli* K12DH1/pTB638 (IFO 14514, FERM BP-1372) obtained in Example 2(2) was digested with restriction enzyme PstI to obtain a DNA fragment of 0.7 kb. The DNA fragment was labeled with $^{32}P$ by the nick translation method (Maniatis et al, supra P109) to give a probe.

The DNA fixed on the filters was hybridized with the labeled probe by reaction in 10 ml of a 5xSSPE (0.9M NaCl, 50 mM sodium phosphate buffer (pH 7.4), 5 mM EDTA), 50% formamide, 5xDenhardt's, 0.1% SDS and 100 µg/ml denatured salmon sperum DNA solution containing the labeled probe. Following the reaction, the filters were washed twice at room temperature for 30 minutes with a 2xSSC(1xSSC=0.15M NaCl, 0.015M sodium citrate) and 0.1% SDS and twice at 68° C. for 30 minutes with a 1xSSC and 0.1% SDS solution. The washed filters were dried and subjected to radioautography for selecting clones capable of reacting with the probe. From the clone λCKR107 was extracted a phage DNA according to the method of Davis et al [Davis et al, "Advanced Bacterial Genetics", Cold Spring Harbor Laboratory (1980)]. This was cleaved with restriction enzyme BglII and EcoRI to obtain a DNA fragment of about 0.5 kb. The DNA fragment was labeled with $^{32}P$ in the same manner as described above. Using the labeled DNA fragment as a probe, hybridization was conducted in the same manner as above. Clones capable of reacting with the probe were singled out. The nucleotide sequences of cDNA regions of several kinds of clones obtained in the above screening were determined by the dideoxynucleotide chain termination method [Messing et al, Nucleic Acids Res. 9, 309(1981)].

Thus, by combining cDNA regions of the thus obtained phage clones, the entire coding region of the rat brain protein kinase C can be covered. An investigation of the amino acid sequence deduced from the DNA sequence reveals that in rat brain protein kinase C there exist at least two molecular types which have 671 [type I (β-1)] and 673 [type II (β-2)]amino acids and which differ only in their C-terminal regions.

Overlapping of the clones thus obtained is illustrated in FIG. 7. The entire DNA sequence and the deduced amino acid sequence are shown in FIG. 8.

(3) Construction of Rat Brain Protein Kinase C Expression Plasmid for Animal Cell Phage clone λCKR152 DNA shown in FIG. 7 was partially digested with restriction enzyme EcoRI to obtain a cDNA of 1.4 Kb. The DNA was mixed with plasmid pTB389 which has been cleaved with restriction enzyme EcoRI and which has been treated with alkaline phosphatase for the removal of its 5' terminal phosphoric acid groups. Plasmid pTB389 is obtained by converting each of the PstI cleavage site at the 5'-terminal region and the BamHI cleavage site at the 3'-terminal region of the interleukin-2 gene region of plasmid pTB106 (disclosed in Japanese Patent Application Laid-Open No. 61-63282, which corresponds to European Patent Publication No. 172,619) to EcoRI, to remove the interleukin-2 gene region. The mixture was reacted with T4 DNA ligase to construct plasmid pTB648. The plasmid pTB648 was then partially digested with EcoRI to obtain a DNA of 4.0 kb having 937 bp of 5'-terminal region of the cDNA, followed by the removal of the 5'-terminal phosphoric acid group. The resulting DNA was mixed with a cDNA of 2.5 kb obtained by partially digesting the phage clone λLCKR107 shown in FIG. 7 with restriction enzyme EcoRI or with a cDNA of 2.3 kb obtained by digesting the phage clone λCKR108 with EcoRI. The mixtures were each reacted with T4 DNA ligase to construct plasmids pTB651 and pTB650, respectively, each of which is to be used for transforming animal cells and covers the entire rat brain protein kinase C encoding region.

Interleukin-2 gene expression vector pTB106 for animal cell (Japanese Patent Application Laid-open No. 61-63282, which corresponds to European Patent Publication No. 172,619) was digested with restriction enzyme HgiAI to obtain a DNA fragment of 1.0 kb containing an interleukin-2 gene leader sequence. The cohesive end of the DNA fragment was converted to flush end with T4 DNA polymerase reaction, to which was linked EcoRI linker CCGGAATTCCGG with T4 DNAligase, followed by complete digestion with EcoRI and HindIII to separate a SV40DNA-derived sequence (promoter and splice portion) and a first DNA fragment of 0.64 kb consisting of the IL-2 gene leader sequence. Separately, the above-described plasmid pTB106 was digested with BamHI and HindIII to separate a DNA replication starting region for replication of a plasmid pBR322-derived DNA in *E. coli* and a second DNA fragment of 2.6 kg having a sequence containing an ampicillin-resistant gene and a SV40DNA-derived polyadenylation region. Further, from plasmid pTB361 (Japanese Patent Application Laid-open No. 61-88881, which corresponds to European Patent Publication No. 177,915) cloned human epidermal cell growth factor (EGF) synthesis gene, a third, EcoRI-BamHI DNA fragment of 0.18 kb coding for human EGF was prepared. The first to third DNA fragments are ligated with T4 DNA ligase reaction to construct plasmid pTB406. The plasmid pTB406 was cleaved at the ClaI and HindIII sites located upstream from the SV40 promoter, into which was inserted a purified ClaI-HindIII DNA fragment of 1.1 kb separated from pTB314 (Japanese Patent Application Laid-open No. 61-63282, which corresponds to European Patent Publication No. 172,619) and having an Abelson murine luekemia virus (A-MuLV) LTR region, thereby to construct plasmid pTB505.

The plasmid pTB505 was further digested with ClaI and BamHI to obtain a DNA fragment of 1.5 kb containing the MuLV-LTR This DNA was mixed with a ClaI-BamHI DNA fragment obtained from the plasmid pTB 650 or pTB651 and the mixture was reacted with T4 DNA ligase to construct plasmid pTB652 and pTB653 having MuLV-LTR at their upstream regions respectively and useful for transforming animal cells (See FIG. 9)

(4) With each of the plasmid pTB652 and plasmid pTB653 obtained in (2) above, *E. coli* K12DH1 was transformed in accordance with the method disclosed in Proc. Natl. Acad. Sci. USA 69, 2110(1972) to obtain a transformant *E. coli* K12DH1/pTB652 (IFO 14539, FERM BP-1373) and a transformant *E. coli* K12DH1/pTB653 (IFO 14540, FERM BP-1374), respectively.

(5) Expression of Rat Brain Protein Kinase C In Animal Cell Monkey COS-7 cell [Cell 27,279–288(1981)] was cultivated on a single layer (5 plastic dishes with Falcon diameter of 100 mm) in DMEM medium supplemented with 5% fetal bovine serum. After replacing with the same medium, the culture was further continued for 4 hours. Then, a calcium phosphate precipitates containing 30 μg/dish of the plasmid pTB652 or pTB653 prepared in the conventional manner [Graham et al, Virology 52, 456(1973)] was added to the cell to obtain cells transfected with pTB652 and pTB653. Four hours later, the cells were treated with glycerol and the cultivation of the pTB652-transfected and pTB653-transfected COS-7 cells was further continued for 70–72 hours. Thereafter, the culture supernatant was discarded and the cells were suspended in 1.5 ml of a buffer [0.25M sucrose, 20 mM Tris-HCl (pH 7.5), 10 mM EGTA, 2 mM EDTA and 20 μg/ml leupeptin] and homogenized by means of a teflon homogenizer. The homogenate was centrifuged at 55000 rpm for 60 minutes with Beckmann 100.2 rotor to obtain a cytoplasmic fraction. The fraction was assayed for protein kinase C activity according to the conventional method [Kikkawa et al, J. Biol. Chem. 257, 13341(1982)] to obtain activity value per 1 mg of the protein. As shown in Table 1 below, the cytoplasmic fractions of the pTB652-transfected and pTB-652-transfected COS-7 cells showed protein kinase C activity of about three times as strong as that of the non-transfected cell.

TABLE 1

| Production of Rat Brain Protein Kinase C with Transfection of Plasmid pTB652 or pTB653 | |
|---|---|
| Transfecting Plasmid DNA | Protein Kinase C Activity in Cytoplasmic Fraction of Transfected Cell (pmole/min/mg) |
| pTB65 | 68.82 |
| pTB653 | 78.30 |
| None | 25.46 |

(6) Analysis of Protein Kinase C Obtained from Transfected Cells

Figure 10:
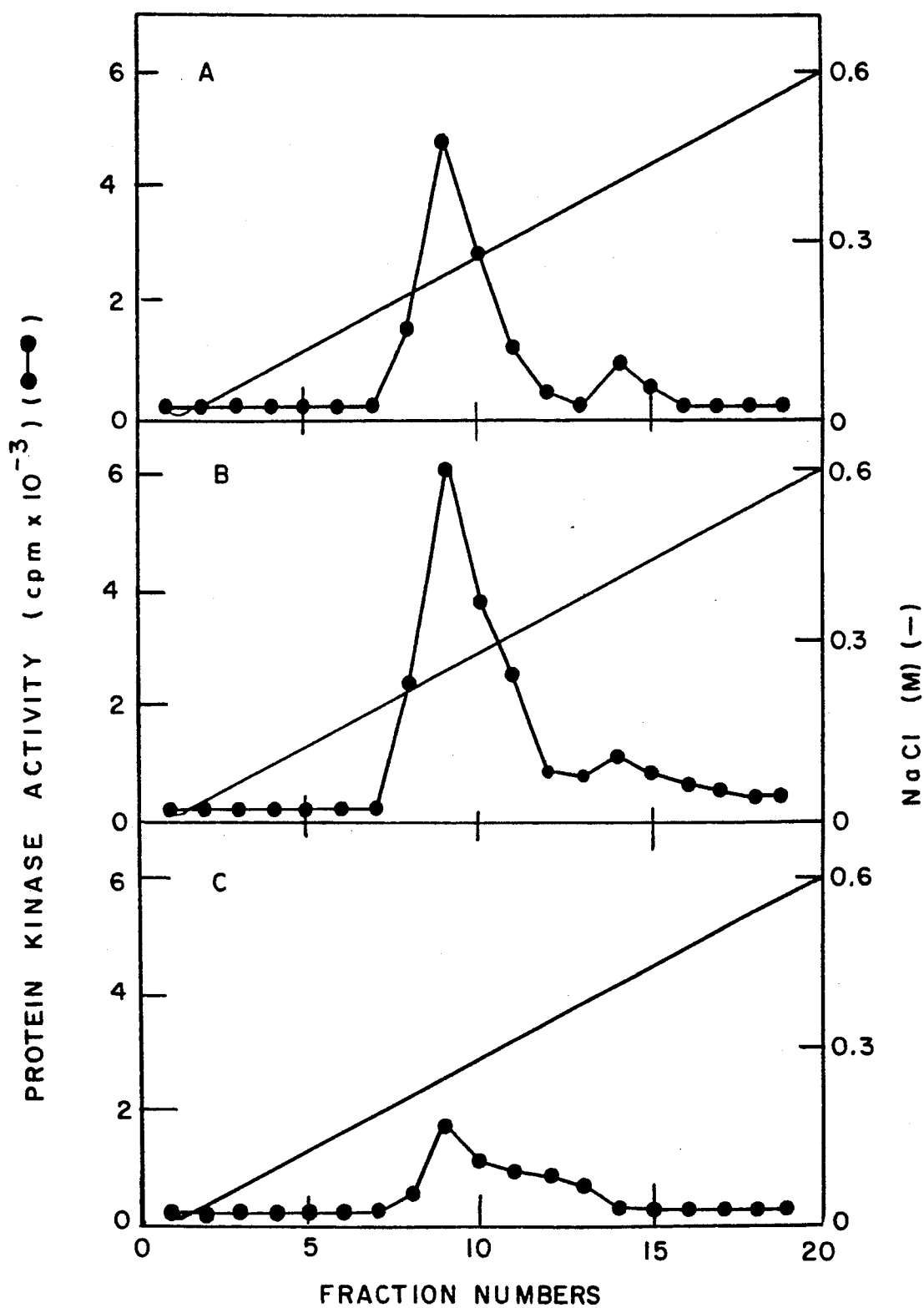
FIG. 10 shows protein kinase C activity pattern in Mono Q column chromatography of cytoplasmic fractions derived from transfected and non-transfected cells, wherein A: pTB652 transfected cell-derived; B: pTB653 transfected cell-derived; C: non-transfected cell-derived.

The cytoplasmic fractions obtained in the manner described above were each diluted with 6 volumes of 20 mM Tris-HCl buffer (buffer A, pH 7.5) containing 0.5 mM EGTA, 0.5 mM EDTA and 10 mM 2-mercaptoethanol and applied on Pharmacia FPLC-Mono Q column (0.5×5 cm, Pharmacia HR5/5). After washing the column with buffer A, protein kinase C was eluted with 20 ml of a linear gradient NaCl (0–0.6M) containing buffer A. As shown in FIG. 10, markedly higher enzyme activity was detected in the test samples from pTB652- or pTB653-transfected cell as compared with the non-transfected cell.

Figure 11:
FIG. 11 shows an autoradiogram of the antibody protein isolated by SDS polyacrylamide gel electrophoresis and reacted with an anti-protein kinase C antibody, wherein a: protein kinase C isolated from rat brains; b: non-transfected cell-derived; c:pTB652 transfected cell-derived; d: pTB653 transfected cell-derived.

The active fractions eluted from the Mono Q column was electrophoresed on 8.5% SDS polyacrylamide gel according to the method of Laemmli [Laemmli, U. K., Nature 227, 680–685 (1970)] and transferred to nitrocellulose filters according to the method of Towbin et al [Towbin, H. et al, Proc. Natl. Acad. Sci. USA 76, 4350–4354(1979)]. The filters were each allowed to stand at 4° C. overnight in a 10 mM Tris-HCl buffer (pH 7.5) containing 150 mM NaCl, 5% casein and 20% normal horse serum and then allowed to stand at room temperature for 1 hour in a 10 mM Tris-HCl buffer (pH 7.5) containing 150 mM NaCl, 1% casein and antiprotein kinase C antibody [obtained from Dr. P. J. Parker; Coussens, L. S., Science 233, 859-866(1986)]. The filters were washed with a 10 mM Tris-HCl buffer (pH 7.5) containing 0.05% Tween 20 and 150 mM NaCl and allowed to stand at room temperature for 1.5 hours in a Tris-HCl buffer containing 1% casein, 150 mM NaCl, 0.1 μCi/ml $^{125}$I protein A. After washing the filters in the same manner as above, X-ray films were exposed to the filters to visualize the protein bands reacted with the antibody. As shown in FIG. 11, the sample derived from the transfected cells gave the protein band reacted with the antibody in the same position as that of protein kinase C isolated from rat brain.

(7) Purification of Protein Kinase C Obtained from Transfected Cells

Similar results were also obtained in the case of COS-7 cells transfected with pTB707 (having a 5'-untranslated region of 55 base pairs) obtained by shortening the 5' untranslated region of pTB652 and with pTB708 (bearing a 5'-untranslated region of 55 base pairs) obtained by shortening the 5' untranslated region of pTB653.

Figure 12:
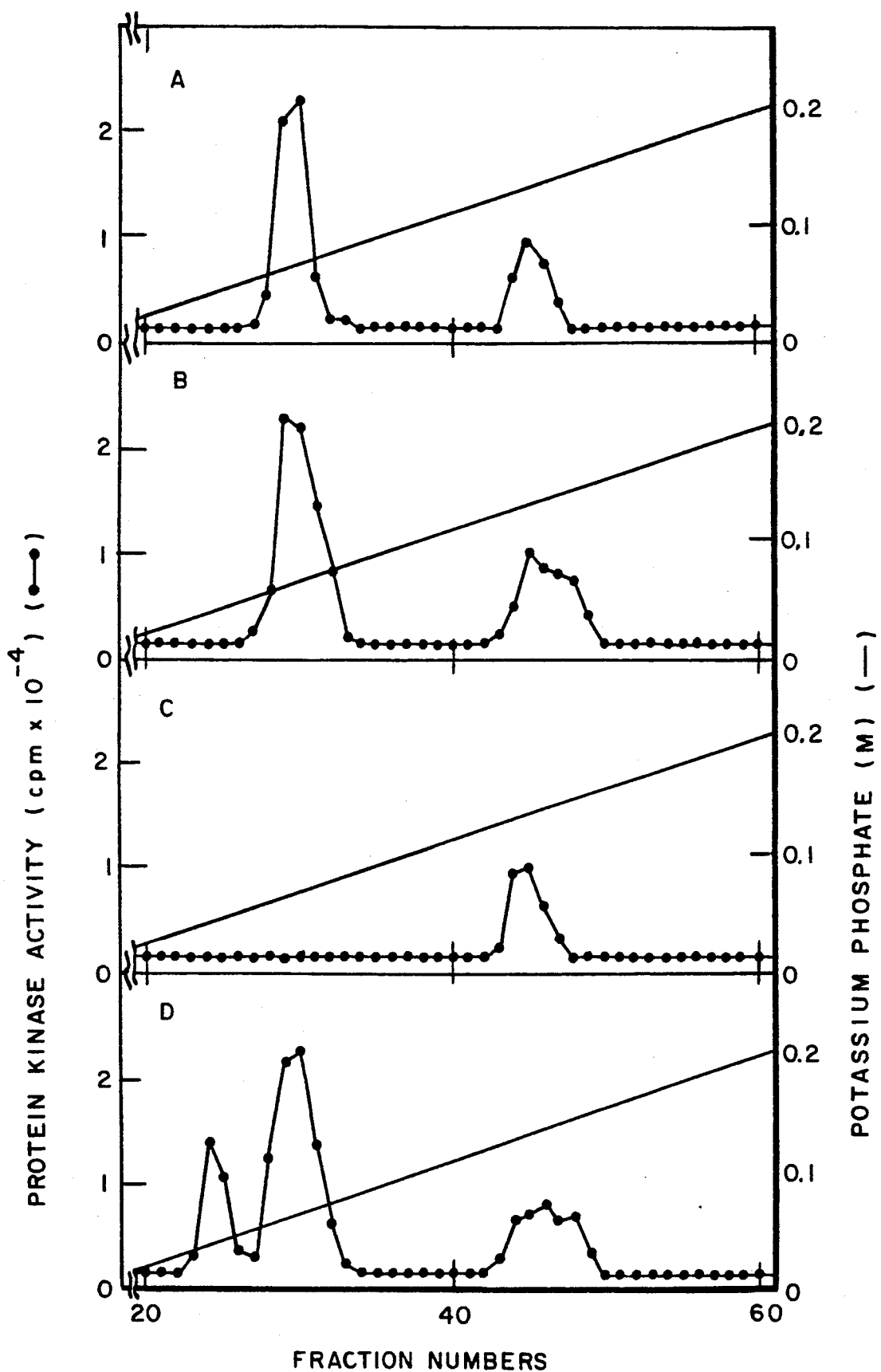
FIG. 12 shows a protein kinase C activity pattern in hydroxylapatite column chromatography of an active fraction on Mono Q column chromatography of cytoplasmic fractions derived from transfected and non-transfected cells, wherein A: pTB707 transfected cell-derived; B: pTB708 transfected cell-derived; C: non-transfected cell-derived; D: rat brain protein kinase C.

Thus, in the same manner as described above, cytoplasmic fractions were obtained from pTB707- and pTB708-transfected cells (each in an amount corresponding to 50 dishes having a 100 mm diameter) and applied to preparatory chromatography using Mono Q column (1×10 cm, Pharmacia HR10/10). The active fractions were partialy purified with a hydroxyapatite column. The active fractions were then diluted with equivolume of a 20 mM potassium phosphate buffer (buffer B, pH 7.5) containing 0.5 mM EGTA, 0.5 mM EDTA, 10% glycerol and 10 mM mercaptoethanol and applied on a hydroxylapatite column (KOKEN Type S, 0.78×10 cm) of Pharmacia FPLC system. The protein kinase C activity was eluted with linear gradient buffer B containing 20-280 mM potassium phosphate. As shown in FIG. 12, the protein kinase C isolated from rat brains gave three peaks (peaks 1, 2 and 3 from the leftside of D in FIG. 12) and the sample derived from the non-transfected cell revealed an activity corresponding to the peak 3.

On the other hand, the sample derived from the transfected cells showed activities corresponding to the peaks 2 and 3. This suggests that the protein kinase C activity corresponding to the peak 2 is expressed by the cell transfected with the plasmid DNA.

EXAMPLE 5

(1) Isolation of Phage Comprising Rat Protein Kinase C III-type (α-type) cDNA and Elucidation of Its DNA Nucleotide Sequence The rat brain mRNA-derived cDNA library which was obtained in Example 4 (1) using *E. coli* C600, HflA as a host was applied to 10 soft agar plates at about 1×10$^5$ clones/plate and transferred to nitrocellulose filters (HATF filter, Milipore Inc.) and lysed with 0.5 N NaOH solution. The resulting exposed and denatured phage DNA was dried for fixation on the plates. In the meantime, an oligonucleotide whose nucleotide sequence (5'TCCGTGACCTCGGCCTTCAGG-TAGAT3') corresponds to the amino acid sequence (amino acids Nos. 162-170) of known bovine protein kinase C α [Parker et al, Science 233, 853-859 (1986)] was chemically synthesized. This oligonucleotide was then labeled with $^{32}$p using T4 polynucleotide kinase and [γ-$^{32}$p]ATP to obtain a screening probe for rat protein kinase C III-type (a-type).

The DNA fixed on the filters was then hybridized with the labeled probe in 10 ml of a 5×SSPE [0.9M NaCl, 50 mM sodium phosphate buffer (pH7.4)], 5×Denhardt's, 0.1% SDS and 100 μg/ml denatured salmon sperum DNA solution containing the labeled probe at 42° C., for 16 hours. Following the reacton, the filters were washed twice at room temperature for 30 minutes with a 6×SSC and 0.1% SDS solution (1×SSC=0.15M NaCl, 0.015M sodium citrate) and twice at 60° C. for 30 minutes with the same solution. The washed filters were dried and subjected to radioautography for selecting clones capable of reacting with the probe. The nucleotide sequence of the cDNA of the thus obtained clone λCKRα5 was determined by the dideoxynucleotide synthesis chain termination method. The nucleotide sequence of the amino acids encoding region of rat protein kinase C III-type (α-type) and the deduced amino acid sequence are shown in FIG. 13.

(2) Expression of Rat protein kinase C III-Type (α-Type) cDNA in An Animal Cell

Figure 14:
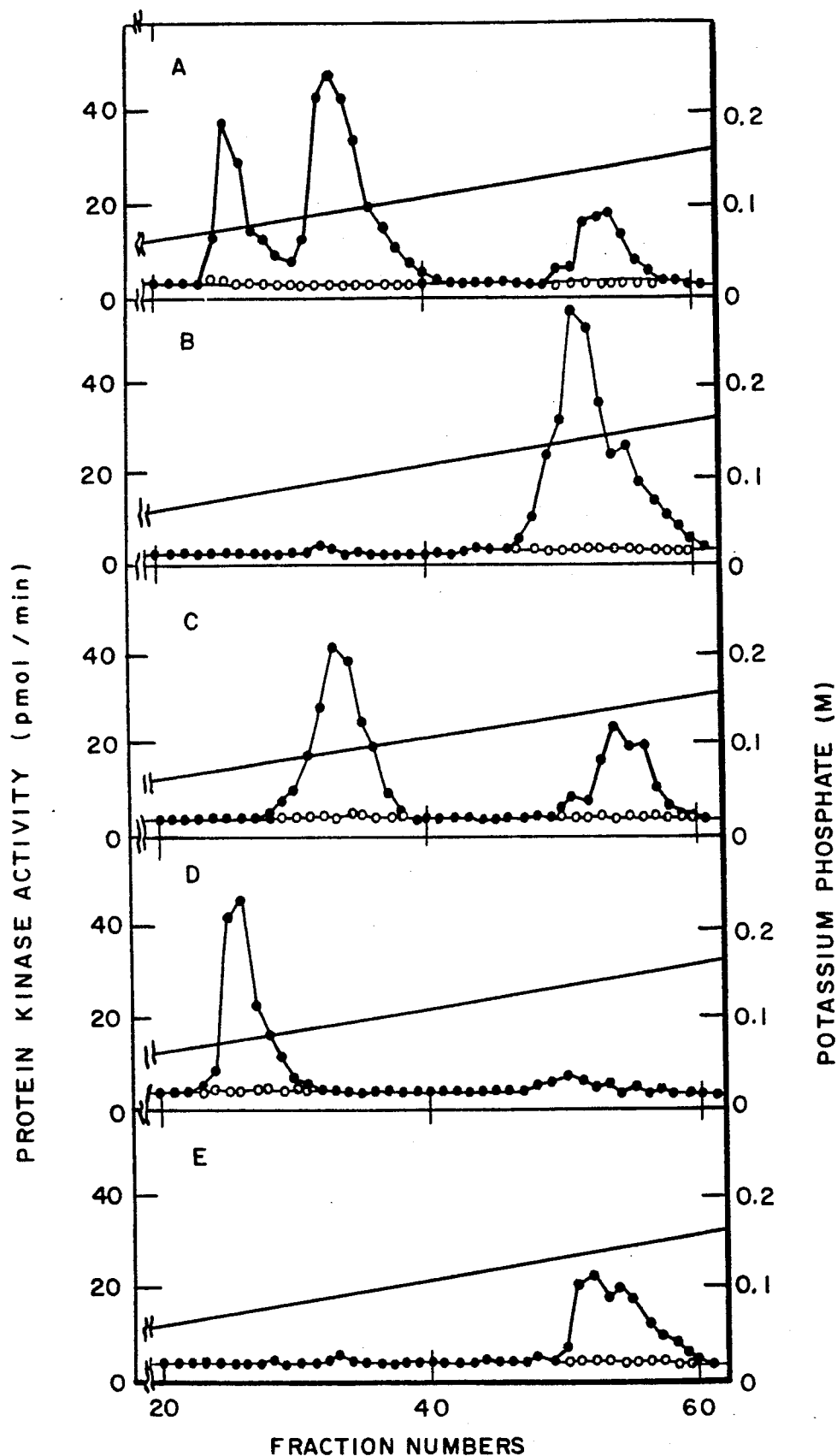
FIG. 14 shows a protein kinase C activity pattern in hydroxylapatite column chromatography of an active fraction on Mono Q column chromatagraphy of cytoplasmic fractions derived from transfected and non-transfected cells; wherein A: rat brain-derived protein kinase C; B: pTB755 transfected cell-derived [protein kinase C III (α type) expression cell-derived]; C: pTB707 transfected cell-derived [protein kinase C I (β-1) expression cell-derived]; D: pTB756 transfected cellderived [protein kinase C γ expression cell-derived [Knopf et al., Cell 46 491-502 ('86)]; and E: non-transfected cell-derived.

Phage clone λCKRα5 was digested with restriction enzyme EcoRI to obtain a cDNA of about 3.1 kb. In the meantime, plasmid pTB652 obtained in Example 4(3) was digested with EcoRI to obtain a DNA fragment of about 4.3 kb from which the cDNA had been removed. These two DNA fragments were ligated with each other using T4 DNA ligase to obtain plasmid pTB755 for use in expression in an animal cell. With this plasmid pTB755 *E. coli* was transformed to obtain a transformant *E. coli* DH1/pTB755 (IFO 14612, FERM BP-1382). Transfection of monkey COS-7 cell was carried out in the same manner as in Example 4(5) using the plasmid pTB755. A cytoplasmic fraction obtained from the transfected cell was subjected to Mono Q column and hydroxylapatite column chromatography in the same manner as described in Example 4(7) to investigate the activity pattern of the expressed rat protein kinase C III-type (α-type) in column chromatography (FIG. 14).

The following references, which are referred to for their disclosures at various points in this application, are incorporated herein by reference.

Cell 46, 491–502 (1986)
Biochemistry 18, 5294 (1979)
Molecular and Cellular Biology 2, 161 (1982)
Molecular and cellular Biology 3, 280 (1980)
Gene 2, 95 (1977)
Gene 4, 121 (1978)
Gene 10, 259 (1982)
Biochemical and Biophysical Research Communication 112, 678 (1983)
Molecular Cloning 239 (1982)
Proc. Natl. Acad. Sci. U.S.A. 60, 160 (1968)
Nucleic Acids Research 9, 309 (1981)
Journal of Molecular Biology 120, 517 (1978)
Journal of Molecular Biology 41, 459 (1969)
Genetics 39, 440 (1954)
Gene 24, 255 (1983)
Journal of Molecular Biology 95, 87 (1984)
Molecular Cloning 249 (1982)
Gene 10, 63 (1980)
Proc. Natl. Acad. Sci. U.S.A. 74, 560 (1977)
Nucleic Acids Research 1, 1513 (1979)
Proc. Natl. Acad. Sci. U.S.A. 69, 2110 (1972)
Gene 17, 107 (1982)
Molecular & General Genetics 168, 111 (1979)
Virology 52, 456 (1973)
Journal of Experiments in Molecular Genetics 431–433 (1972)
Proc. Natl. Acad. Sci. U.S.A. 77, 4505 (1980)
Science 122, 501 (1952)
Virology 8, 396 (1959)
The Journal of the American Medical Association 199, 519 (1967)
Proceeding of the Society for the Biological Medicine 73, 1 (1950)
J. Biol. Chem 257, 13341 (1982)
Proc. Natl. Acad. Sci. USA 69, 1408 (1972)
Proc. Natl. Acad. Sci. USA 72, 3961 (1975)

Molecular Cloning 309 (1982)
Molecular Cloning 382 (1982)
J. Mol. Bil. 113, 237 (1977)
DNA Cloning, A Practial Approach, p49 (1985)
Molecular Cloning 320 (1982)
Advanced Bacterial Genetics (1980)
Japanese Patent Application Laid-Open No. 61-63282
European Patent Publication No. 172,619
Japanese Patent Application Laid-open No. 61-88881
European Patent Publication No. 177,915
Nature 227, 680-685 (1970)
Proc. Natl. Acad. Sci. USA 76, 4350–4354
Science 233, 859–866 (1986)

We claim:

1. A substantially pure human protein kinase C which is a polypeptide comprising the following amino acid sequence:

Tyr-Ser-Ala-Gly-Gly-Asp-Leu-Met-Leu-His-Ile-His-Ser-Asp -Val-Phe-Ser-Glu-Pro-Arg-Ala-Ile-Phe-Try-Ser-Ala-Cys-Val -Val-Leu-Gly-Leu-Gln-Phe-Leu-His-Glu-His-Lys-Ile-Val-Tyr -Arg-Asp-Leu-Lys-Leu-Asp-Asn-Leu-Leu-Leu-Asp-Thr-Glu-Gly -Tyr-Val-Lys-Ile-Ala-Asp-Phe-Gly-Leu-Cys-Lys-Glu-Gly-Met -Gly-Tyr-Gly-Asp-Arg-Thr-Ser-Thr-Phe-Cys-Gly-Thr.

2. A substantially pure rat protein kinase C which is a polypeptide comprising amino acid residues 1-224 of the 673 or 671 amino acid sequence shown in FIG. 8 or a polypeptide consisting essentially of the sequence of amino acid residues of FIG. 13.

3. A substantially pure recombinant rat protein kinase C according to claim 2 further comprising amino acid residues 225-621 of the amino acid sequence shown in FIG. 8.

4. A rat protein kinase C according to claim 3 further comprising the following amino acid sequence:

622
ArgAspLysArgAspThrSerAsnPheAspLysGluPheThrArgGlnProVal
GluLeuThrProThrAspLysLeuPheIleMetAsnLeuAspGlnAsnGluPhe
AlaGlyPheSerTyrThrAsnProGluPheValIleAsnVal.
671

5. A rat protein kinase C according to claim 3 further comprising the following amino acid sequence:

622
CysGlyArgAsnAlaGluAsnPheAspArgPhePheThrArgHisProProVal
LeuThrProProAspGlnGluValIleArgAsnIleAspGlnSerGluPheGlu
GlyPheSerPheValAsnSerGluPheLeuLysProGluValLysSer.
673

6. The human protein kinase C of claim 1, wherein the polypeptide is a recombinant polypeptide.

7. The rat protein kinase C of claim 2, wherein the polypeptide is a recombinant polypeptide.

* * * * *